(12) United States Patent
Atkin

(10) Patent No.: US 9,023,278 B2
(45) Date of Patent: May 5, 2015

(54) INSTRUMENTATION SYSTEMS AND METHODS

(76) Inventor: Micah James Atkin, Glen Huntly (AU)

( * ) Notice: Subject to any disclaimer, the term of this patent is extended or adjusted under 35 U.S.C. 154(b) by 1151 days.

(21) Appl. No.: 12/160,569

(22) PCT Filed: Jan. 11, 2007

(86) PCT No.: PCT/AU2007/000012
§ 371 (c)(1),
(2), (4) Date: Sep. 26, 2008

(87) PCT Pub. No.: WO2007/079530
PCT Pub. Date: Jul. 19, 2007

(65) Prior Publication Data
US 2009/0041626 A1 Feb. 12, 2009

Related U.S. Application Data

(60) Provisional application No. 60/758,199, filed on Jan. 12, 2006.

(30) Foreign Application Priority Data

Jan. 12, 2006 (AU) .................. 2006900139

(51) Int. Cl.
*G01N 21/00* (2006.01)
*B01L 3/00* (2006.01)
*G01N 35/00* (2006.01)

(52) U.S. Cl.
CPC ....... *B01L 3/502715* (2013.01); *B01L 2200/10* (2013.01); *B01L 2200/143* (2013.01); *B01L 2200/148* (2013.01); *B01L 2300/022* (2013.01); *B01L 2300/023* (2013.01); *B01L 2300/024* (2013.01); *B01L 2300/027* (2013.01); *B01L 2300/0627* (2013.01); *B01L 2300/0816* (2013.01); *B01L 2400/0487* (2013.01); *G01N 35/00732* (2013.01); *G01N 35/00871* (2013.01)

(58) Field of Classification Search
USPC ........ 600/532; 422/408, 63–67; 436/164, 518
See application file for complete search history.

(56) References Cited

U.S. PATENT DOCUMENTS

| | | | |
|---|---|---|---|
| 4,755,660 A | 7/1988 | Nakano | |
| 6,054,277 A * | 4/2000 | Furcht et al. | 435/6.11 |
| 6,166,370 A * | 12/2000 | Sayag | 250/221 |
| 6,454,173 B2 | 9/2002 | Graves | |
| 6,495,104 B1 | 12/2002 | Unno et al. | |
| 6,969,357 B1 * | 11/2005 | Colman et al. | 600/529 |
| 2003/0216660 A1 * | 11/2003 | Ben-Oren et al. | 600/532 |
| 2004/0220498 A1 * | 11/2004 | Li et al. | 600/584 |

FOREIGN PATENT DOCUMENTS

| | | |
|---|---|---|
| WO | 93/19363 | 9/1993 |
| WO | 03/036270 | 5/2003 |

* cited by examiner

Primary Examiner — Jyoti Nagpaul

(57) ABSTRACT

A device (600) for performing at least part of an analytical process comprises a communicator (605) to facilitate communication with the device, and a data handler (610) to handle data of the analytical process and/or the device. In an embodiment, the device (600) is a consumable device and/or a microfluidic device. A method for performing at least part of an analytical process using a device comprises the steps of: (a) introducing a sample into the device; (b) handling data associated with the test using a data handler of the device; and (c) facilitating communications about the test using a communicator of the device. In another embodiment, the method is performed using a consumable device and/or a microfluidic device.

15 Claims, 35 Drawing Sheets

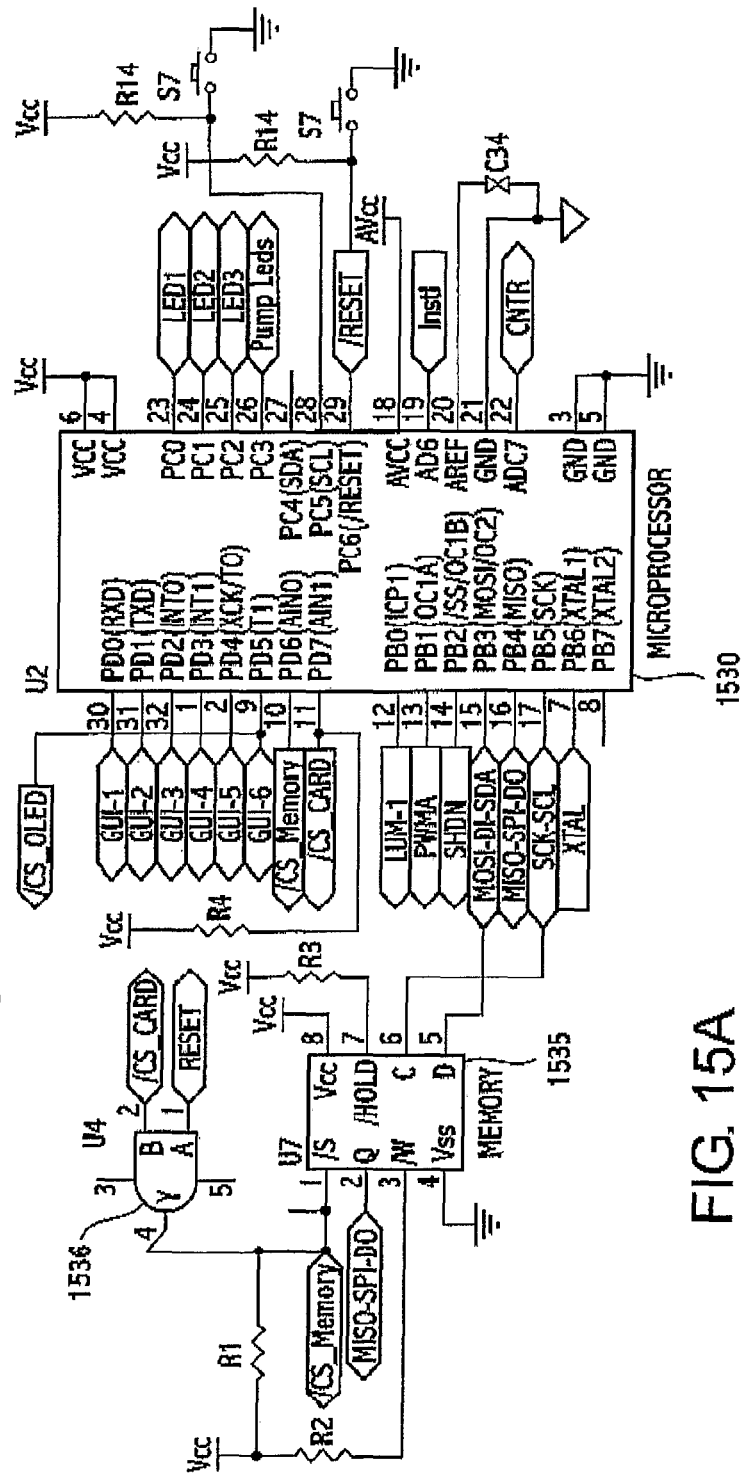

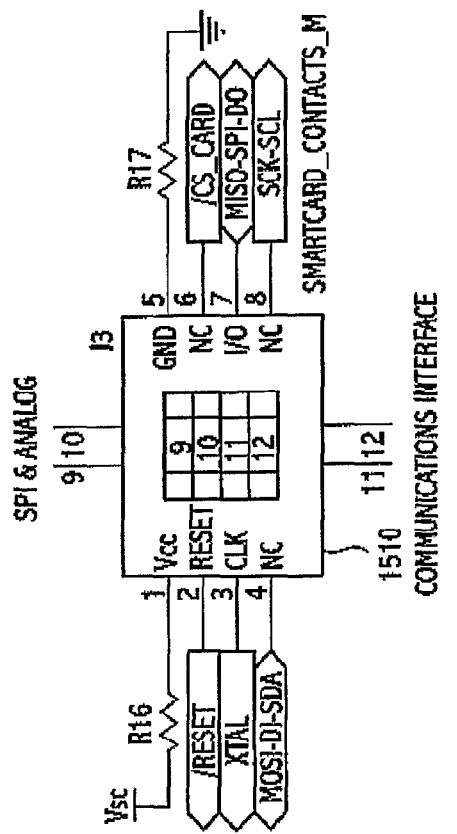
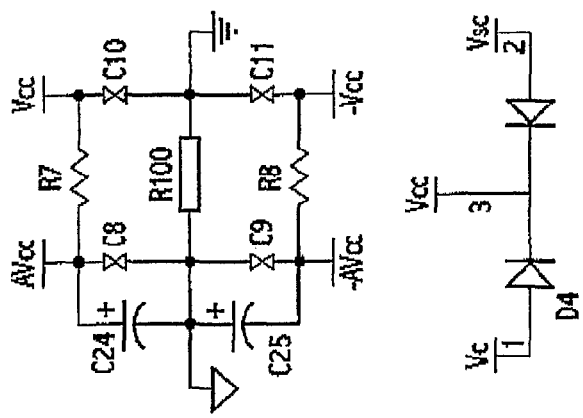
FIG. 15B

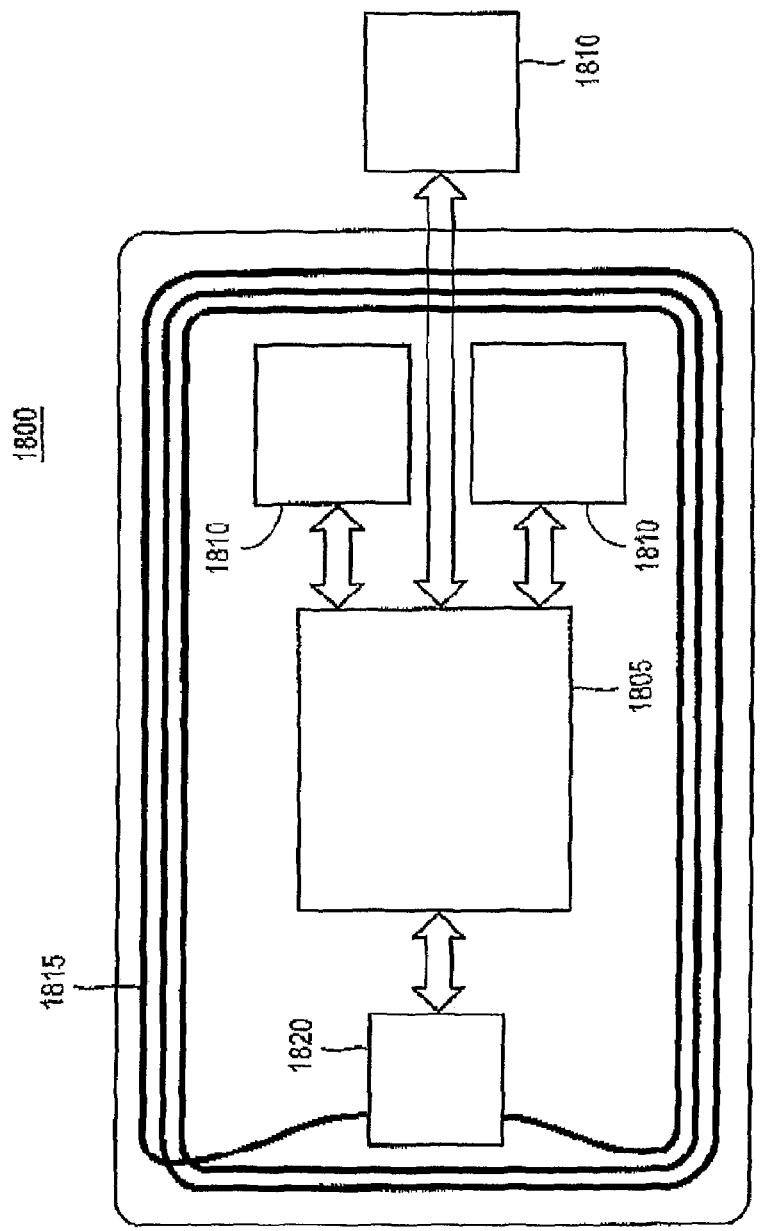

INSTRUMENTATION SYSTEMS AND METHODS

CROSS-REFERENCE TO RELATED APPLICATIONS

This application is the National Stage of International Application No. PCT/AU2007/000012, filed Jan. 11, 2007, which claims priority to U.S. Provisional Application No. 60/758,199, Jan. 12, 2006 and Australian Application No. 2006900139, Jan. 12, 2006.

FIELD OF THE INVENTION

This invention relates generally to systems and methods for performing at least one part of an analytical process.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

Instruments of many different configurations are known. For example, certain types of instruments control experiments or collect information from an environment or unit or material(s) under test. By way of example only, such instruments include digital multimeters, oscilloscopes, DNA sequencers, pressure sensors, temperature sensors, pH sensors, or the like.

Historically, instrumentation has developed from the use of discrete instruments that are dedicated to a single function and manually operated, such as a centrifuge or spectrophotometer, to instrumentation systems that integrate multiple processes. Such multiple process instruments typically require complicated or multi-step procedures be manually performed by a user to operate the individual instruments. In some cases, discrete instrument systems have been combined and automated in an effort to reduce costs and increase productivity. Examples of such combined instruments include the integration of large liquid handling robotic workstations. FIG. 1 illustrates a block diagram of an exemplary system 100 having a fully reusable instrument 110 that contains all operational components (e.g., user interface, CPU/control systems, detector systems, process controllers, fluid handling, data storage, and power module).

To reduce sample cross contamination, the fixed sample handling components of some instruments, such as the plumbing and fluid containers, have been replaced in many applications with disposable components, such as plastic tubing, well plates, and centrifuge tubes.

Increasing interest in the development of micro-scale systems for the integration of instrumentation components has been brought about by the many advantages of miniaturisation. In particular, performance improvements can be achieved over traditional laboratory equipment in terms of automation, reproducibility, speed, cost and size.

Polymer-based microfluidic components have been developed as a cost effective alternative to silicon for simple, disposable components in instrumentation systems. However, these systems have been limited in complexity and the degree of integration because they involve externally driven fluid-handling components, sensors, and actuators. U.S. Pat. Nos. 6,900,889, 6,810,713 and 6,408,878, and U.S. Patent Application Publications 2004/209354A and 2002/0148992A1 illustrate implementations of such systems. FIG. 2 illustrates a block, diagram of an exemplary system 200 that includes a reusable instrument 210, containing all operational components (e.g., user interface, CPU/control systems, detector systems, process controllers, data storage, and power module) except for fluid-handling components, which are located on a removable consumable device 205.

Polymer-based microfluidic devices which incorporate on-board sensors and actuators that interface to external instrumentation have also been developed, such as those described in U.S. Pat. Nos. 6,073,482, 6,896,778 and 6,103,033. The limitations of such devices include reliability, problems relating to the interface to connectors and problems associated with long interconnects (e.g., electromagnetic interference and susceptibility, line impedance, packaging and device size).

Smart Card polymer devices are known that contain memory modules and, in some cases, central processing units (CPU's) for use in personal identification, security, and payment applications. Examples of such Smart Cards are described in the ISO 7816 and ISO 7501 standards for identification cards, ISO 14443, ISO 10536, and ISO 15693 standards for RFID cards from the International Organization for Standardization, and GSM 11.11 from the Global System for Mobile Telecommunications standard. Smart Cards can be classified according to the type of chip they contain and type of interface they use to communicate with an external instrument. Generally, there are three different types of chips associated with Smart Cards grouped according to the functionality they provide, including memory-only, wired logic, and microcontroller based Smart Cards.

Memory-only Smart Cards include serial protected memory cards. Such cards provide for data storage capabilities, in a manner similar to magnetic stripe cards, but have greater data storage capacity and can be used with a lower cost reading device than magnetic-based cards. Memory-only Smart Cards do not contain logic or perform calculations, however, and simply store data with some cards also having data protection features.

Wired-logic Smart Cards contain a logic-based state machine that provides encryption and authenticated access to card memory and its contents. Wired-logic Smart Cards have a static file system supporting multiple applications, with optional encrypted access to memory contents, but the command set and file structure associated with these cards can only be changed by redesigning the integrated circuit (IC) on the card. FIG. 3 illustrates a block diagram of an exemplary system 300 that includes an instrument 310, which interfaces with a Chip Card 305, containing logic and data storage.

Microcontroller Smart Cards, commonly referred to as "Smart Cards," contain a microcontroller with an operating system. The microcontroller executes logic, performs calculations and stores data in accordance with its operating system and on-board memory can be updated many times. FIG. 4 illustrates a block diagram of an exemplary system 400 that includes an instrument 410, which interfaces with a Smart Card 405, containing a CPU and data storage.

All of these types of Smart Cards require an external instrumentation interface to operate that can be categorised as a contact or contact-less interface depending on how the electrical connection is implemented. Smart Cards may offer both types of interfaces by using two separate chips (sometimes called "hybrid cards") or a dual-interface chip.

Smart Cards with internal power supplies are known, and thin film batteries for such cards are currently being developed. Smart Cards with internal power supplies have been described for memory storage, such as for backup applications. For example, U.S. Pat. No. 6,854,657 describes a twin battery configuration for field programmable Smart Cards allowing the use of volatile memory.

Smart Card devices for autonomous operation are also known. For example, "Super Smart Cards" that incorporate graphical user interface (GUI) and interactive elements have been demonstrated and generally incorporate microprocessor, memory, battery, liquid crystal display (LCD) and membrane keypad components. Although these devices show increased functionality over the standard Chip and Smart Cards, none have been demonstrated with sensor or actuator control or with fluidic component integration.

Smart Cards with on-board biometric fingerprint sensor interfaces are known for use in some security applications. For example, U.S. Pat. No. 6,848,617 describes a fingerprint sensor module for insertion into a Smart Card, and U.S. Pat. No. 6,325,285 describes a Smart Card containing memory, microprocessor, input/output (I/O) and fingerprint biometric sensor components. International Patent Application Publication WO00161638A1 describes a more generic Smart Card for biometric sensing that is interfaced to internal or external sensors for measuring data, but because the device includes no provisions for actuator operation or sensor control or feedback, the device functionality is limited to basic sensor data acquisition.

U.S. Pat. No. 6,454,708 describes another example of a Smart Card operating as part of a sensor system. The Smart Card is interfaced to an electrocardiogram (ECG) device on a patient such that ECG data is collected and stored on the card before transporting the card to an external instrument for monitoring and processing. This configuration is limited in that it applies to ECG data measurement only and, even though some of the interface electronics may be placed on-board the card, the card only stores the acquired ECG data.

Additionally, U.S. Pat. No. 6,896,778 describes using a blank Smart Card chip carrier module with an electrode having a semipermeable membrane in direct contact with an internal fluidic channel. However, this device does not provide for any on-chip electronics or integrated circuits interfaced to sensor or actuator components, allowing for only very limited automation and integration with an external instrument. U.S. Patent Application 2005/0031490 describes a sensor chip on a smart card electrode module, wherein the silicon sensor chip contains its own integrated electrode array with multiplexer and amplifier, and the sensor chip is encapsulated to have the sensitive area exposed to fluid and its electrical connections associated with the smart card electrode module. Although, like U.S. Pat. No. 6,896,778, the system described in U.S. Patent Application 2005/0031490 is still limited to this single architecture of the sensor chip directly connected to the smart card interface.

Low-cost disposable Radio Frequency Identification (RFID) labels, called "Smart Labels," have been incorporated with sensor circuits for monitoring purposes. For example, U.S. Patent Application Publication 2005/0088299 describes an RFID based sensor network, which acquires sensor data wirelessly through a reader and communicates with another instrument for processing the data, and U.S. Patent Application Publication 2005/174236 describes an RFID system, which comprises a transceiver, sensor system, and interface to identify, track and acquire the operational history of a product during its life cycle. Both of these device configurations are limited in operation to responding to an external reader, which interrogates and provides power to the RFID sensor systems, and to providing only sensor and RFID data for processing by the external system. Further, U.S. Patent Application Publication 2005/0248455 describes an RFID sensor system that is limited to monitoring time and temperature to determine the freshness, or shelf life, of perishable items. While this device can periodically reactivate from a low power state to perform a monitoring function, it still requires communication to an external device upon interrogation.

Memory components have been incorporated into polymer-based microfluidic components for instrumentation systems, in which full control and monitoring are provided by an external instrument. FIG. 5 illustrates a block diagram of an exemplary instrumentation system 500 containing all operational components (e.g., user interface. CPU/control systems, detector systems, process controllers, and power module), except for fluid-handling components, which are located on a removable consumable device 505 with data storage capability.

For example, U.S. Patent Application Publication 2004/0248318 describes a removable biochip on a chip card with read/write-able memory, but provides no direct interface between the fluid or on-chip sensors or actuators. Thus, this configuration performs only a memory operation, and the fluidic component must be removed for processing with external instruments. Similarly, U.S. Pat. No. 6,153,085, U.S. Patent Application Publications 2002/155033A1 and 2005/0019213, and International Patent Application Publications WO 2003/082730A and WO 2004/112946 describe microfluidic systems incorporating memory components, but these devices are limited in that they incorporate only memory-based circuit components and include no self-operation capability and no electronic sensor or fluidic system interface on the device. Thus, such devices must operate interfaced with external instruments and are therefore limited by the associated interconnect problems. Further, such devices cannot perform autonomous or even semi-autonomous operations and provide no sensor and/or actuator monitoring, control, feedback, or signal enhancement.

SUMMARY OF THE INVENTION

In one embodiment, a device for performing at least part of an analytical process comprises a communicator to facilitate communication with the device, and a data handler to handle data of the analytical process and/or the device. In another embodiment, the device is a consumable device and/or a microfluidic device.

In another embodiment, a device for performing at least part of an analytical process comprises a consumable device that includes a communicator configured to facilitate communication with the device, at least one sensor or actuator pertaining to the analytical process and/or the device, and a data handler configured to handle acquired data.

In another embodiment, a device for performing at least part of an analytical process comprises a consumable device that includes a communicator configured to facilitate communication with the device, at least one sample storage or handling element, and a data handler configured to handle the acquired data.

In another alternative embodiment, a device for performing at least part of an analytical process comprises a microfluidic device that includes a communicator configured to facilitate communication with the device and a data handler configured to handle data of the analytical process.

In an embodiment, a method for performing at least part of an analytical process using a device comprises the steps of: (a) introducing a sample into the device; (b) handling data associated with the test using a data handler of the device; and (c) facilitating communications about the test using a communicator of the device. In another embodiment, the method is performed using a consumable device and/or a microfluidic device.

BRIEF DESCRIPTION OF DRAWINGS

Other objects and advantages of the present disclosure will become apparent to those skilled in the relevant art(s) upon reading the following detailed description of preferred embodiments, in conjunction with the accompanying drawings, in which like reference numerals have been used to designate like elements.

FIGS. 15A-15E illustrate a circuit diagram, representation of an autonomous device similar to the device illustrated in FIGS. 14A-E.

FIG. 18 is a diagram representing an exemplary device that includes RFID, electronic circuit, and sensor components.

DETAILED DESCRIPTION OF THE INVENTION

Overview

Figure 6A:
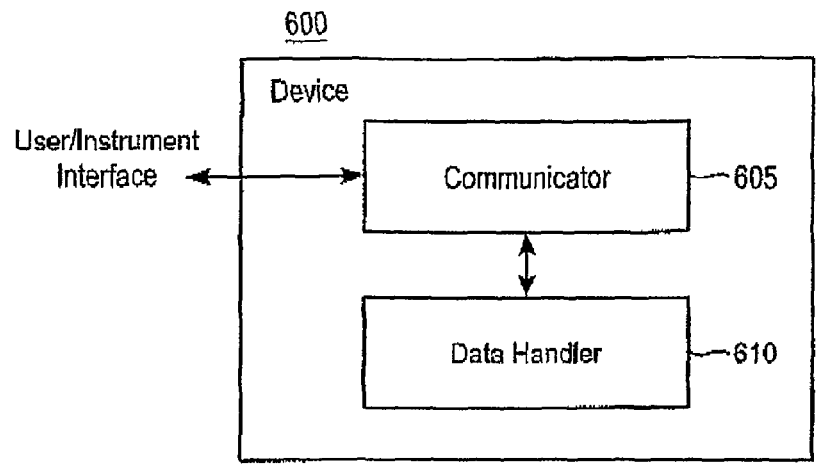
FIG. 6A is a high-level block diagram representing an exemplary device for performing at least part of an analytical process, in accordance with an embodiment of the present invention.

FIG. 6A illustrates an exemplary device 600 for performing at least part of an analytical process. As used herein, the term "part of an analytical process" refers to any suitable function that can be performed by the device 600, including, but not limited to, data storage, sample storage and testing functions, such as physical, chemical and/or biochemical processing, monitoring, and/or analysis.

In an embodiment, the device 600 can comprise a consumable device. As used herein, the term "consumable" describes a device that is consumed or used up after a single use or a definable series of uses (such as, for example, serial blood glucose measurement). Typically a consumable device will either be disposed of after such usage is complete, or may be stored for later reference (for example, in the field of forensic science). In another embodiment, the device 600 can comprise a microfluidic device. As used herein, the term "microfluidic" refers to fluid handling, manipulation, or processing carried out in structures having at least one dimension less than about one millimeter. In a further embodiment, a microfluidic device comprises non-Smart Card formatted electrodes and can also include one or more sensors.

In further embodiments, devices can incorporate electrodes in a similar format to Smart Card electrodes. The electrodes may be of any suitable type, for example, the electrodes may conform to the dimensions of the electrode chip carrier module of the ISO 7816-2 specification. FIG. 6C shows a plan view of an exemplary six-electrode contact 612

Figure 6B:
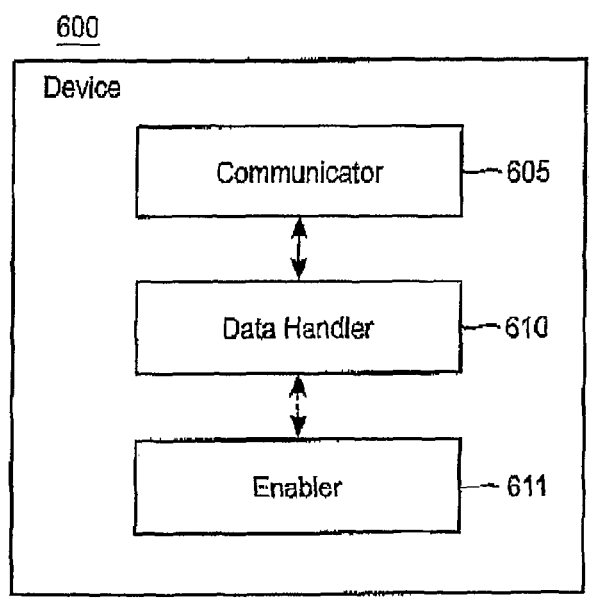
FIG. 6B is a high-level block diagram of an exemplary device that includes an optional enabler component.
Figure 6C:
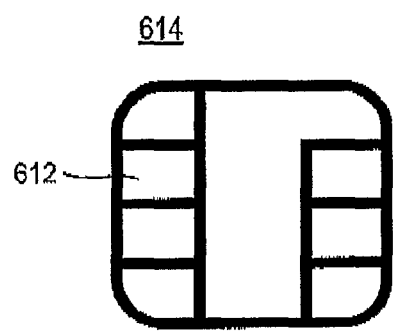
FIG. 6C shows a plan view of an exemplary electrode contact Smart Card module.
Figure 6D:
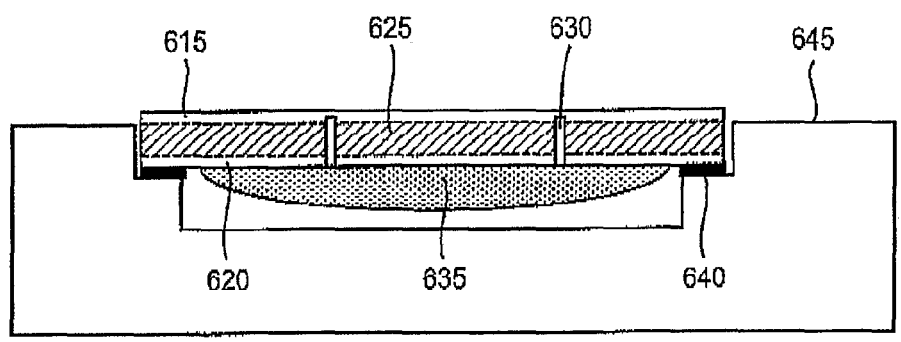
FIG. 6D shows a cross-sectional view of the exemplary electrode contact Smart Card module of FIG. 6C.

Smart Card module 614, and FIG. 6D shows a cross-sectional view of the module 614, shown, in FIG. 6C. Typically, the electrodes 612 can comprise gold coated conductive layers 615 and 620 on either side of a polymer carrier layer 625 and can be connected by vias 630, as shown in FIG. 6D. One side of the module 614 can contain an encapsulated silicon integrated circuit 635, and the entire module 614 can be bonded into a plastic housing 645 with an adhesive 640. In other embodiments, devices can incorporate electrodes in a format other than a Smart Card electrode format.

The device 600 may include a data handler 610 configured to handle data of the analytical process. The data handler can take any suitable form. In one embodiment, the data handler comprises an electronic circuit and/or an integrated circuit, including, but not limited to, an analog conditioning circuit, digital circuit, memory, and CPU. Additionally, the data handler can perform any required data handling function, including, but not limited to, monitoring, controlling, collecting, storing, manipulating or transmitting data. As used herein, the term "data" refers to any useful information in any form. For example, the data may be electromagnetic, visual, analog, digital, audio, etc.

Optionally, as shown in FIG. 6B, the device 600 may include an enabler 611, which may or may not be coupled to the data handler 610. The enabler 611 can be considered part of an analytic process. For example, the enabler 611 may include a sample interactive element, sample storage media (e.g., an absorbent medium, blister pack, wells, etc.), or a microfluidic element, among other elements.

The device 600 may also include a communicator 605 configured to enable communication to and/or from the device 600. The device 600 can communicate with any suitable thing, including, but not limited to, a user/person, an instrument, another device, and a network. In an embodiment, the communicator 605 comprises a user interface that can include inputs (e.g., push buttons, voice/sound recognition, vibrations recognition, reed switches, and capacitance, among other inputs) and outputs (e.g., OLED, LCD, color change, or some other visual display mechanism, among other outputs). In an embodiment, the communicator 605 comprises an instrument interface that can include, for example, electrodes or a Smart Card electrode module, among other implementations. The communicator 605 can communicate via any suitable means, including, but not limited to, electromagnetic waves (whether or not via a physical connection), sound, light, touch (e.g., by a user depressing a button), and pressure.

The device 600 may further include any other suitable components, such as, components for storing and/or processing a sample, sensors for measuring parameters (e.g., biometric sensors), actuators (e.g., for controlling at least a portion of the analytical process), controllers, feedback paths, signal conditioning elements, and RFID components, among others.

The device 600 can be made from any suitable material, including, but not limited to, polymer, metal, paper, glass, or composite materials. Composite materials may, for example, include a polymer, metal, ceramic, paper or silicon material. In one embodiment, the device 600 substantially comprises non-silicon material. In another embodiment, the device 600 comprises a polymer or a composite material.

The device 600 can have dimensions less than about 100 mm×150 mm×20 mm. In another embodiment, the device 600 can have dimensions less than about 70 mm×120 mm×10 mm. In a further embodiment, the device 600 can have dimensions of about 60 mm×90 mm×5 mm. In yet another embodiment, the device 600 can have dimensions of about the size of a credit card.

The device 600 may be externally powered or self-powered using any suitable means. For example, batteries, internal galvanic cells, biometric, capacitive, inductive, kinetic, piezoelectric, and solar energy harvesting/storage means can be used to self-power the device.

A detailed description of devices for performing at least part of an analytical process and methods for using such devices is presented below. The explanation will be by way of exemplary embodiments to which the present invention is not necessarily limited.

Data Handler Component

The device 600 for performing at least part of analytical process may comprise the data handler 610 for handling data of the analytical process, as shown in FIG. 6A. In an embodiment, the data handler 610 comprises electronic and/or integrated circuit elements, including, but not limited to, one or more analog, digital, power, radio frequency (RF) and/or microwave circuits implemented using discrete and/or integrated circuit components. For example, a simple data handler 610 may comprise an analog circuit capable of measuring and controlling a sensor interfaced to an instrument. In this case, the data handler 610 may comprise a phototransistor interface to an operational amplifier integrated circuit, providing signal conditioning terminating to a connector on the device 600 for interface to an instrument.

In another embodiment, the data handler 610 can comprise various computing elements, including, but not limited to, integrated circuits containing microprocessors or microcontrollers. In this case, the integrated circuits may contain an operating system, for example, versions and derivates of Linux, Microsoft Windows, PC/SC, OCF, and Java.

In another alternative embodiment, the data handler 610 comprises electronic and/or integrated circuits that can operate independently and/or interface to an external device, including, but not limited to, an instrument and another device. In this embodiment, the data handler 610 may be capable of user or instrument interaction prior to, during or after use of the device 600. For example, the data handler 610 may be capable of providing useful data, including, but not limited to, data relating to one or more of device history, usage, expiry, manufacturing, program security, operation security, user profile, calibration, results, user instructions, instrument instructions or parameters, monitoring of device usage and/or expiry, functionality of reagents or components, user interaction, device operational parameters, environmental conditions, location information, and device operational progress.

Figure 1:
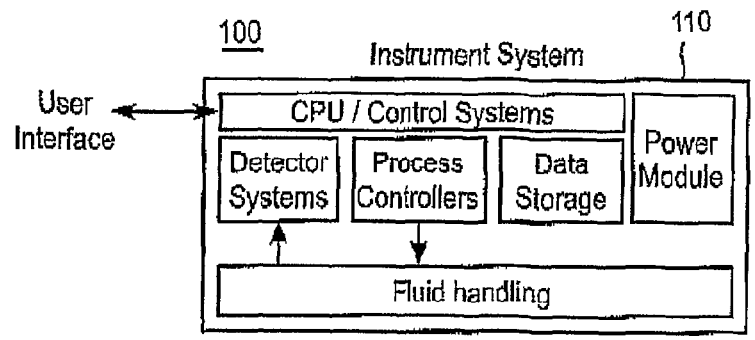
FIG. 1 is a block diagram representing an exemplary system that includes a reusable instrument containing all operational components.
Figure 2:
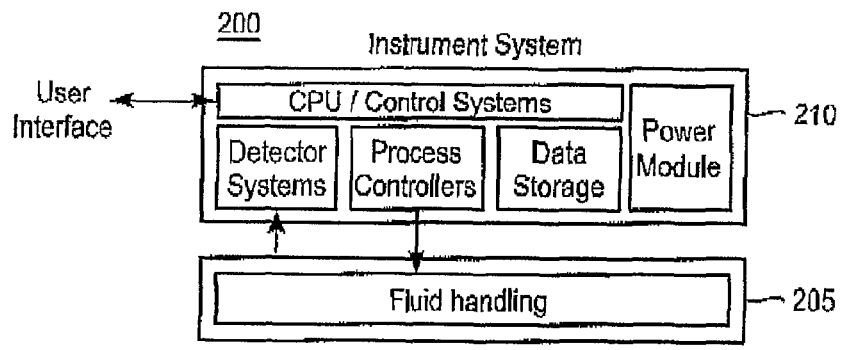
FIG. 2 is a block diagram representing an exemplary system that includes a reusable instrument containing all but fluid-handling operational components, which are located on a consumable device.
Figure 3:
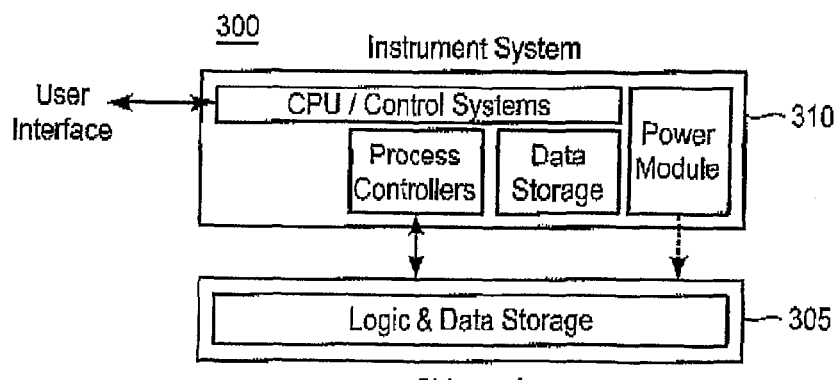
FIG. 3 is a block diagram representing an exemplary Chip Card instrumentation system.
Figure 4:
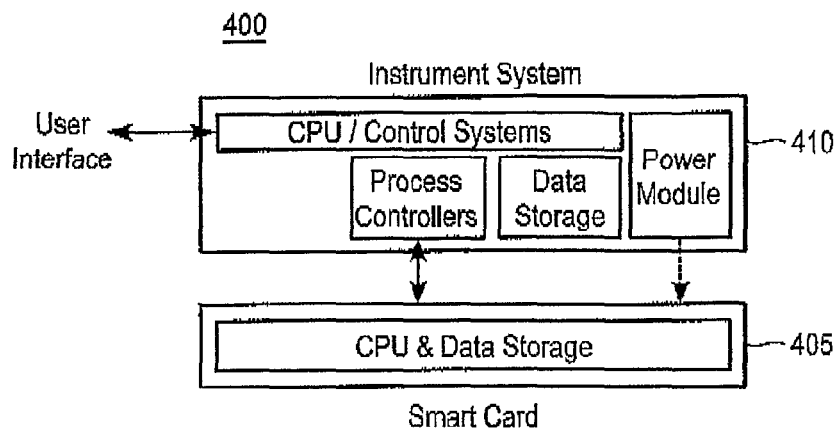
FIG. 4 is a block diagram representing an exemplary Smart Card instrumentation system.
Figure 5:
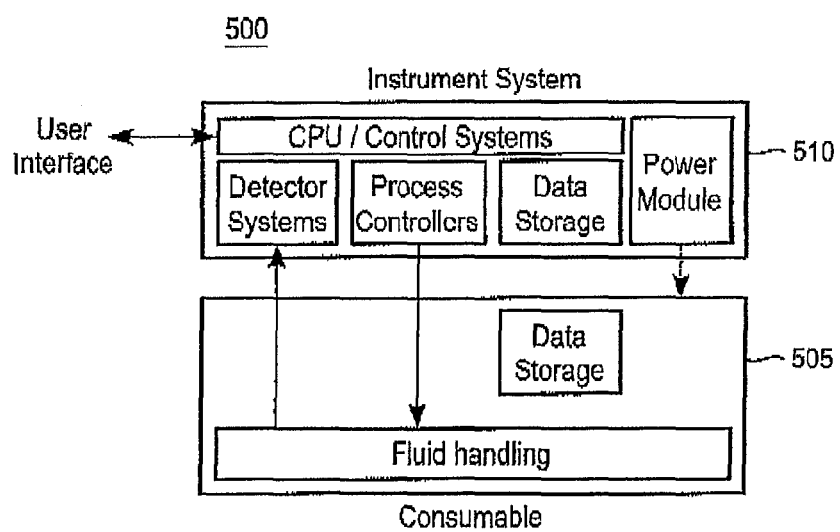
FIG. 5 is a block diagram representing an exemplary system that includes an instrument and a removable consumable device with data storage capability.

In another illustrative embodiment, the electronic circuit and/or integrated circuits of the data handler 610 may operate in a "slave" configuration, in which case the device 600 is interfaced with an external instrument or another device that provides control over the device 600. For example, FIGS. 3 and 4 depict exemplary Chip Card and Smart Card devices 305 and 405, which may operate in a slave configuration by responding to external commands from instruments 310 and 410, respectively.

Figure 8:
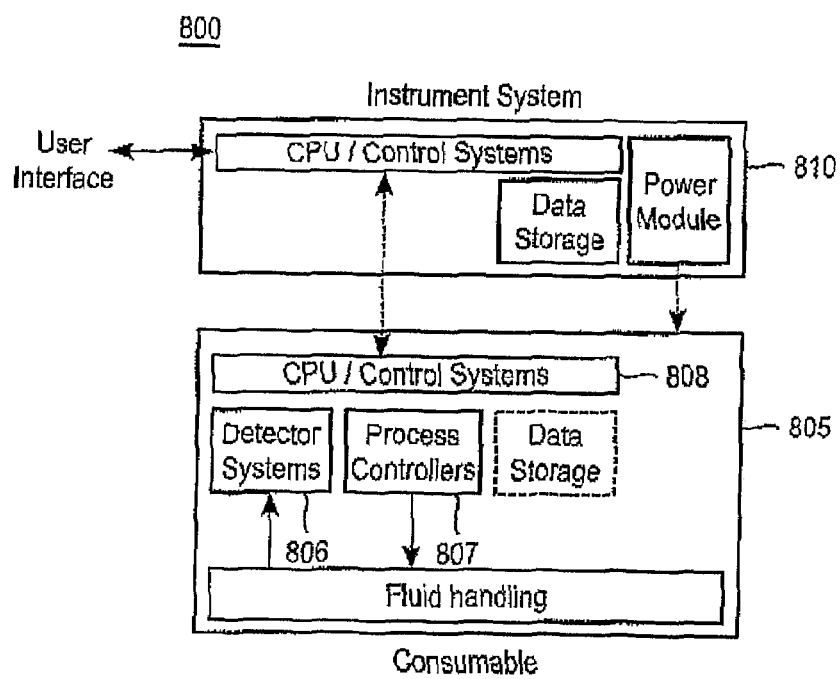
FIG. 8 is a block diagram representing an exemplary system that includes a consumable device having integrated sensors and/or actuators and processing and/or control systems capability, and an instrument providing power and communication for system operation and user interface.
Figure 9:
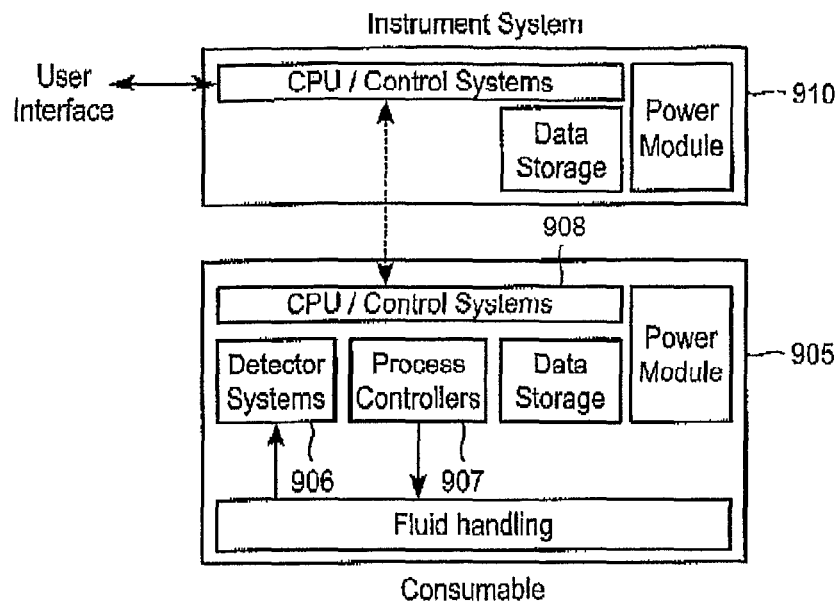
FIG. 9 is a block diagram representing an exemplary system that includes a consumable device having integrated sensors and/or actuators, processing and/or control systems capability, and a power supply.
Figure 10:
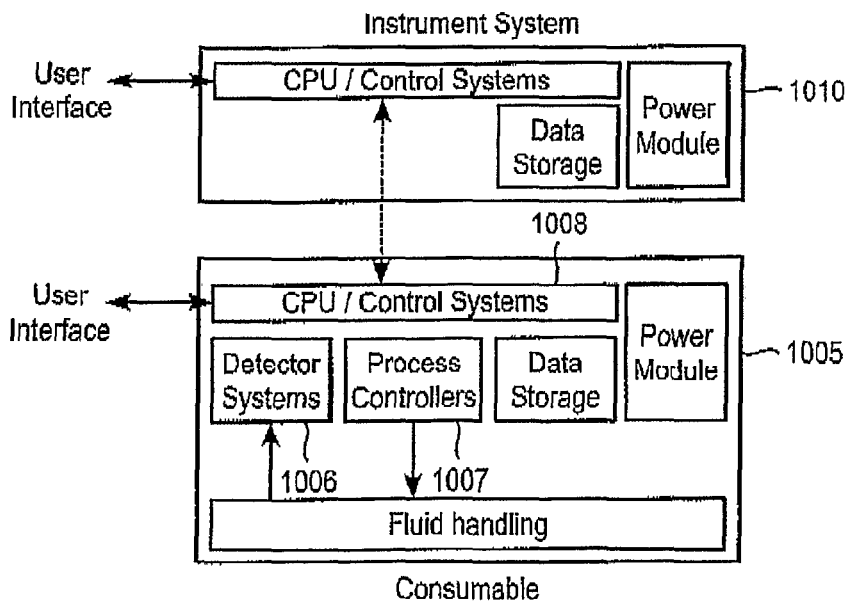
FIG. 10 is a block diagram representing an exemplary system that includes a consumable device having integrated sensors and/or actuators, processing and/or control systems capability, and a user interface allowing direct interaction with the consumable device.
Figure 11:
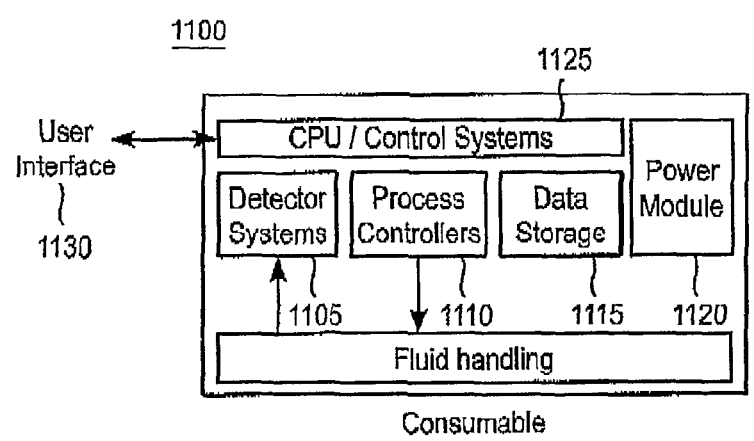
FIG. 11 is a block diagram representing an exemplary self-contained consumable device instrumentation system, in which all necessary components for device operation are integrated onto the consumable device.

In another embodiment, the electronic circuit and/or integrated circuits of the data handler 610 may operate in a "master" configuration, in which case the device 600 is capable of independent operation and/or decision-making and/or can control communication with other devices. For example, FIG. 11 depicts an exemplary device 1100, which is a self-contained device capable of independent operation. FIGS. 8-10 depict exemplary devices 805, 905 and 1005 that are interfaced to external instruments 810, 910 and 1010 and are also capable of operating in a master configuration.

Integration of data handling components onto a device can enable localized control, monitoring, processing, and/or storage of data to simplify use, reduce size of instrumentation, reduce costs, improve reproducibility, reliability, performance, safety, security and quality control. Further, testing costs can be reduced in many applications, including point-of-test applications, in which cost, size, and complexity of current testing procedures can otherwise be substantial.

On-board data handling components can simplify user operation, for example, by providing improved signal response, such as providing an LED or output in place of a chemical colorimetric response. User operation can also be simplified by partially or fully automating operation or by providing data to an instrument in the form of an indication of device functionality. User operation can also be simplified by allowing storage of data, which enables user profiling, improved automation and simplified operation.

On-board data handling components can reduce size of instrumentation and costs. For example, the use of circuitry on a device enables integration of functionality into the device, thereby reducing instrumentation requirements, resulting in a reduction in instrumentation size and, in some cases, eliminating the need for an instrument altogether. Further, costs associated with instrument expenditure and instrument operation can be reduced by using data handling components with functionality that simplifies instrumentation design, and automates operation.

On-board data handling components can improve reproducibility, for example, by improving device quality control (QC), increasing sensor and actuator performance, and monitoring experimental conditions and user interactions.

On-board data handling components can also improve performance. For example, use of localised feedback, control, and signal conditioning can improve sensor and/or actuator performance and help overcome interconnection issues by increasing signal response and reducing electromagnetic interference and susceptibility of the components. On-board calibration and verification procedures can also be implemented to improve system response by characterising sensor performance and/or adjusting sensor results. Further, on-board data handling components can enable communication between devices for data transfer between an instrument and/or other devices. The use of communication protocols between devices improves correct signal transmission, and enables transmission of multiple values through a single connection. Such communication protocols can replace the need to rely on traditional transmission of raw sensor signals through individual connections, which requires multiple lines for multiple parameters and is susceptible to electromagnetic interferences. Examples of communications protocols include, but are not limited to, RS232, I²C, SPI, USB, ISO 14443, Ethernet, TCP/IP, GSM, GPRS, and Near Field Communication.

On-board data handling components can improve user safety, for example, by providing warnings or altering operational parameters of the device under certain conditions. Such functionality enables QC monitoring. Such monitoring can relate to historical or current conditions of the device including, but not limited to, QC tracking (e.g., of manufacturing parameters), component status, environmental conditions, operator usage, and shelf life. For example, QC monitoring can be used to disable a test if the device is no longer within operational tolerance, has been contaminated, or if operational conditions are exceeded during an experiment (e.g., if a test protocol is not adhered to). Further, storage of parameters, such as manufacturing data, experimental conditions, results, and/or other pertinent data on the device can simplify tracking and traceability for many applications by maintaining a record with the device. The data handler may perform QC functions on the device and/or an external instrument to reduce the need for external testing and improve the reliability of the device and its experimental operation.

On-board data handling components can improve user security, for example, by restricting access to data, ensuring authorised operation of the device or an external instrument, and providing product security for a device manufacturer. For example, access to or use of the device or the instrument may be restricted under certain conditions (e.g., if data is not entered correctly) or during certain periods of operation (e.g., before or during a critical point in a testing procedure). Other security functions may be implemented, such as, warning systems, data verification, encryption and dongle protection. International Patent Application PCT/IB2006/003311 describes exemplary product security functions that can be implemented.

On-board data handling components can enable firmware/software and hardware upgrades to be automatically installed from a device, so that the device acts as a source of upgrades for an external instrument. Such upgrades are typically provided as new software versions or service packs on disc media, but are provided relatively infrequently (i.e., for major revisions/upgrades only) due to costs associated with frequent distribution of upgrade media and problems associated with user installation. Further, some installation upgrades can be performed remotely via the world-wide-web, but only if the instrument is connected to an appropriate network.

Thus, providing some or all of the upgrade information with a device can automate the upgrading process, eliminating the need to install upgraded software from other media and, consequently, simplifying user operation and reducing overhead costs associated with production and distribution of upgrade media. For example, certain aspects of traditionally instrument-specific hardware and software can be incorporated directly onto the device. In this way, a new device can simply be provided that enables tire upgraded functionality without the equipment downtime, logistical difficulties, and costs associated with manually upgrading or replacing the instrument hardware or software.

Universal Instrument Approach

The incorporation of communicators and data handlers in the devices described herein can enable sophisticated interactions between the devices and instruments. In one embodiment, an instrument can comprise an instruction module to receive and process instructions from a device in communication with it. This configuration allows the device to provide information to the instrument about its functionality, including, for example, information according to U.S. Pat. No. 6,495,104 and International Patent Application PCT/IB2006/003311. Providing information about the device functionality enables the application of a "generic" or "universal" instrument, in which one instrument can be used for a wide variety of applications and the device can provide the instrument with application specific data or indicate which data on the instrument is to be used.

In one embodiment, the instrument can contain program code to perform its internal, operations (such as acquiring data, controlling sensors and actuators, selecting acquisition channels, pumping, switching valves, setting temperatures), as well as program flow and GUI templates. The device can provide data to enable instrument operations by configuring the program flow and GUI templates for a particular application. This approach allows a single instrument to be capable of performing analysis for a wide variety of applications. When this approach is combined with careful system integration (i.e., by careful choice of system components to be split between the instrument and the device), an almost universal instrument can be implemented. For example, some or all of the sensor, actuator, detection and or control systems can be located on the device and a common electrical/optical/physical interface can be provided on the instrument.

In one embodiment, the device includes not only a sensor but also the corresponding interface electronics that, provide feedback, control, signal processing, and/or calibration information. Incorporating signal processing capabilities onto the device can enable autonomous and/or semi-autonomous operation. Such capabilities can be important for many field and low-cost applications, where cost and/or size of traditional equipment limits their use. The low-cost miniature instrumentation systems described herein may be used as an independent instrument interfaced to a user or another instrument, but operating autonomously. They may also operate semi-autonomously by communicating with other instruments. By way of example only, a semi-autonomous device may process data and operate sensors and/or actuators interfaced on the device, but accept commands and pass results to an interfaced instrument.

Communicator Component

The device 600 for performing at least part of analytical process preferably comprises a communicator 605 to facilitate communication with the device 600, as shown in FIG. 6A. The communicator 605 may comprise at least one of a user interface or an instrument interface, and the communicator 605 may be adapted to communicate one or more of (a) device settings or operational information, (b) application information, (c) information on part of the analytical process, or (d) instructions to the user.

In an embodiment, the communicator 605 comprises a user interface and may communicate with one or more of (a) the data handler 610, (b) an instrument, (c) a sensor, or (d) an actuator. The communicator 605 of the device 600 may contain display elements to assist in operation. In this case, any suitable display elements may be used, for example, LCD, organic light-emitting diode (OLEDs), LEDs, and electroluminescent, fluorescent, and incandescent displays. In addition, the display elements may comprise observable events, such as permanent or non-permanent changes in heat and electromagnetic, electrostatic, colour, reflectivity and liquid volume changes, among others.

In another embodiment, the communicator 605 comprises an instrument interface, including any suitable interface between the device 600 and an instrument. Examples of suitable interface mechanisms include electrical contacts, acoustic and ultrasonic vibration, mechanical, magnetic, radio frequency, microwave, and optical energy. Communication between the device and an instrument or another device may involve contact or contact-less interface mechanisms.

In another embodiment the device comprises a Smart Card electrode module which may, for example, communicate via a contact or contact-less interface. For example, FIGS. 12A, 12E, 13A and 13E illustrate exemplary devices 1200 and 1300 that include chip-card electrode modules 1240 and 1350, respectively.

DETAILED DESCRIPTION OF EXEMPLARY IMPLEMENTATIONS

According to an optional aspect of the present invention, a device for performing at least part of an analytical process comprises on-board data handling components, including at least one integrated circuit component optionally interfaced to one or more sensor or actuator components. The sensor or actuator component(s) can optionally (a) take measurements, (b) control at least one portion of an analytical process, (c) enable feedback to an instrument via the data handling components, or (d) comprise signal conditioning elements.

According to another optional aspect of the present invention, a device for performing at least part of an analytical process comprises on-board data handling components, including an electronic and/or integrated circuit, which can operate in a slave or master configuration, and fluid-handling structures generally having at least one dimension less than about ten millimeters, but can be less than about one millimeter. By way of example only, such fluid handling structures might include lateral flow strips, channels, microchannels, tubing, wells, reservoirs, and absorbent materials.

Figure 7:
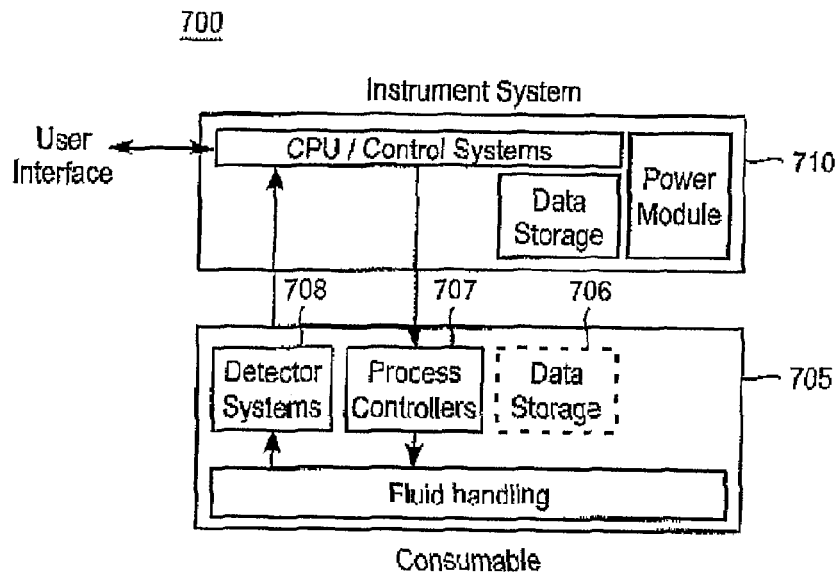
FIG. 7 is a block diagram representing an exemplary system that includes a consumable device having integrated sensors and/or actuators and optional data storage and power modules, and an instrument providing processing and control systems for their operation.

In one exemplary implementation, a device according to the present disclosure comprises on-board data handling components that include electronic and/or integrated circuits for connecting sensors and/or actuators to one or more external devices. For example, FIG. 7 illustrates a block diagram of a system 700 that includes a consumable device 705 operating in a slave configuration with respect to an instrument 710. The consumable device 705 contains on-board data handling circuitry comprising memory 706, logic, and digital and/or analog circuits 707 and 708, as well sensor and actuator components, which are part of systems 708 and 707, respectively. A communicator (not shown) of the consumable device 705 provides an interface with the instrument 710, which performs computing, user interface, and control and monitoring functions.

Figure 12A:
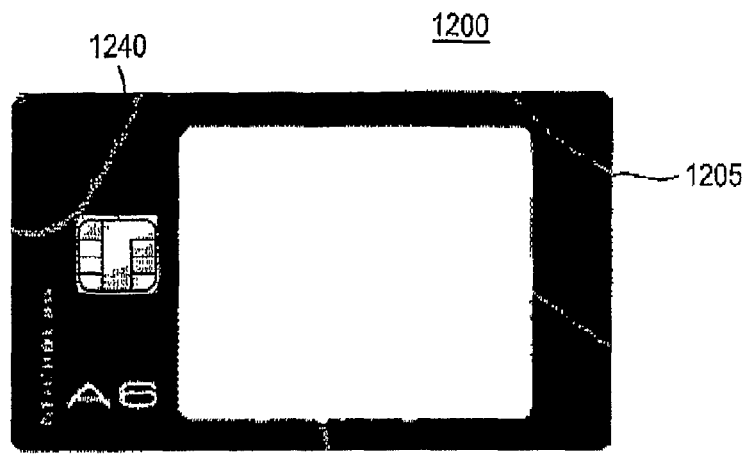
FIGS. 12A-E illustrate composite images of a multilayer device that interfaces with an instrument to form a system similar to the system shown in FIG. 7.
Figure 12B:
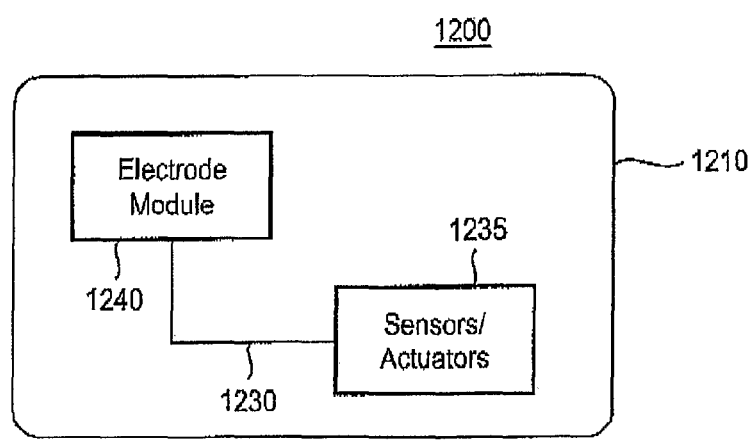
Figure 12C:
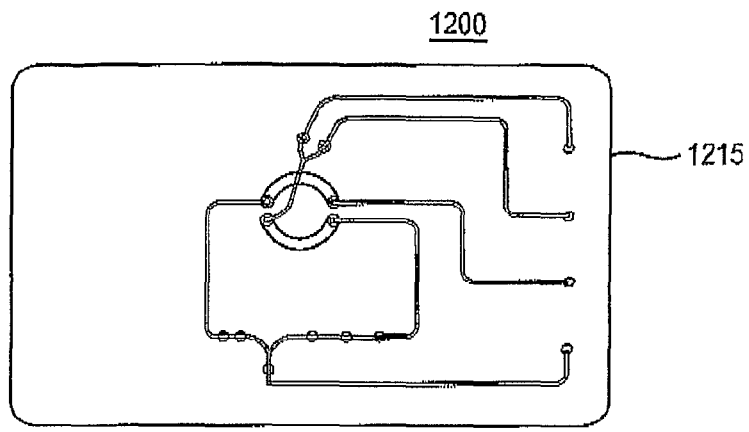
Figure 12D:
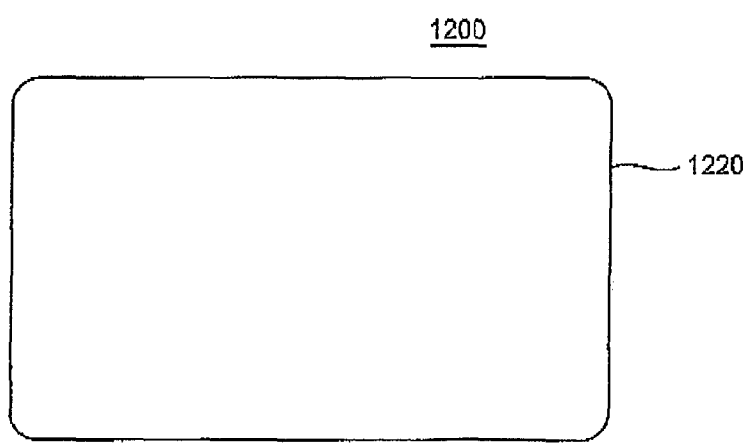
Figure 12E:
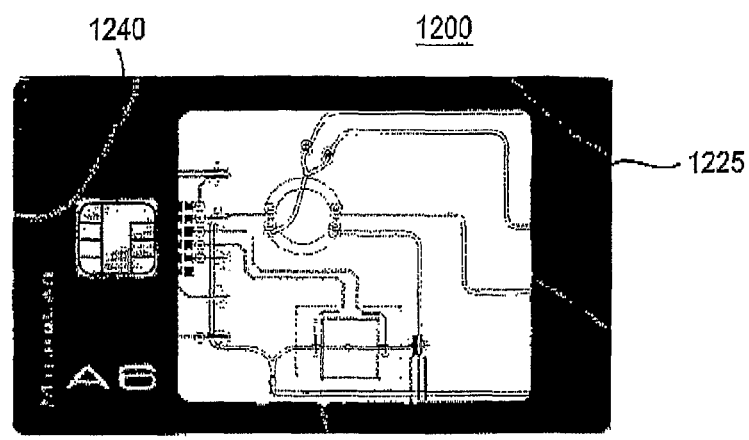

FIGS. 12A-12E illustrate composite images of a consumable device 1200 fabricated by multilayered components and having a configuration similar to the consumable device 705, shown in FIG. 7. FIG. 12A illustrates top graphic and interface layers 1205, FIG. 12B shows electrical layers 1210, FIG. 12C shows fluidic layers 1215, FIG. 12D shows bottom, layers 1220, and FIG. 12E shows atop view of all layers 1225, as assembled. In this example, analog signal and control lines 1230 are connected directly to sensors and actuators 1235 on the device. The sensors and actuators 1235 are interfaced to chip card electrodes 1240, which, in turn, are interfaced to an instrument when communicating with a Smart Card electrode module, which may or may not have an integrated circuit on it.

In another exemplary implementation, a device according to the present invention comprises on-board data handling components that include electronic and/or integrated circuits that connect sensors and/or actuators to signal processing and control elements interfaced to one or more external devices. For example, FIGS. 8-10 illustrate block diagrams of systems 800, 900 and 1000 that include consumable devices 805, 905 and 1005 comprising on-board data handling components, including detection components 806, 906 and 1006 and process controllers 807, 907 and 1007, in addition to control systems and/or microprocessors 808, 908 and 1008. Communicators (not shown) of the consumable devices 805, 905 and 1005 provide interfaces with instruments 810, 910 and 1010, respectively.

Figure 13A:
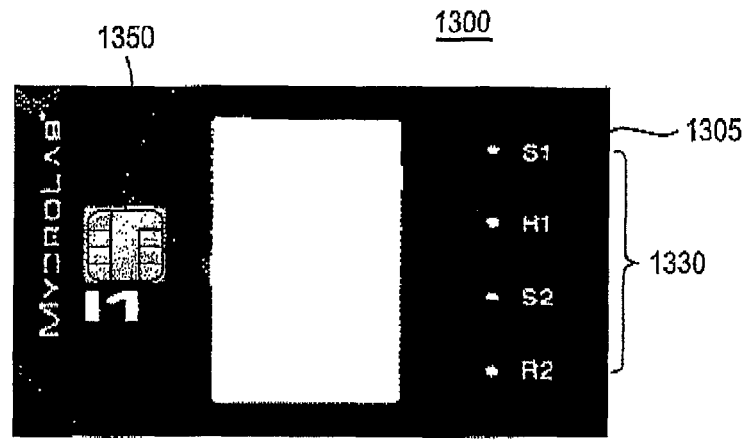
FIGS. 13A-E illustrate composite images of a multilayer device that interfaces with an instrument to form a system similar to the system shown in FIG. 8.
Figure 13B:
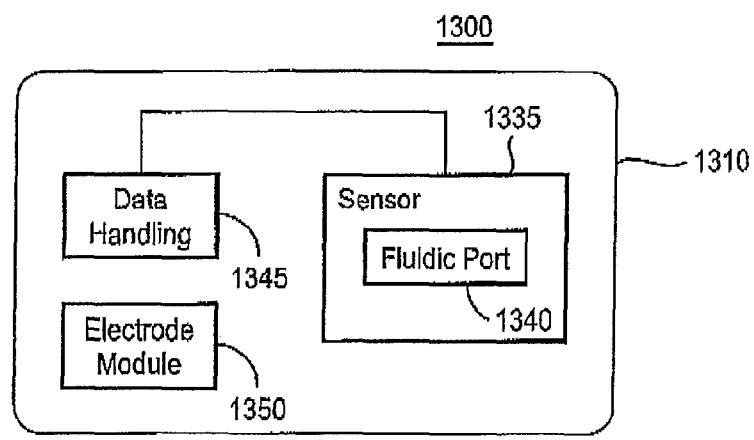
Figure 13C:
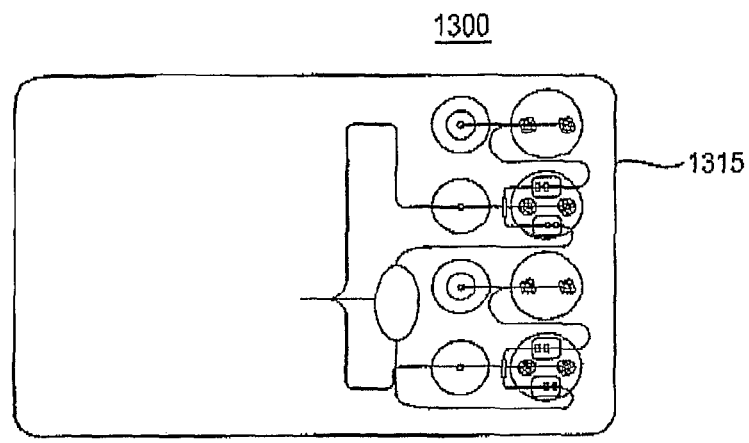
Figure 13D:
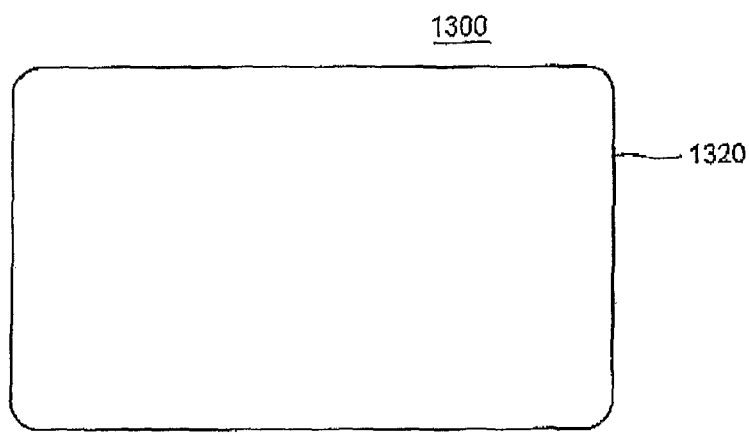
Figure 13E:
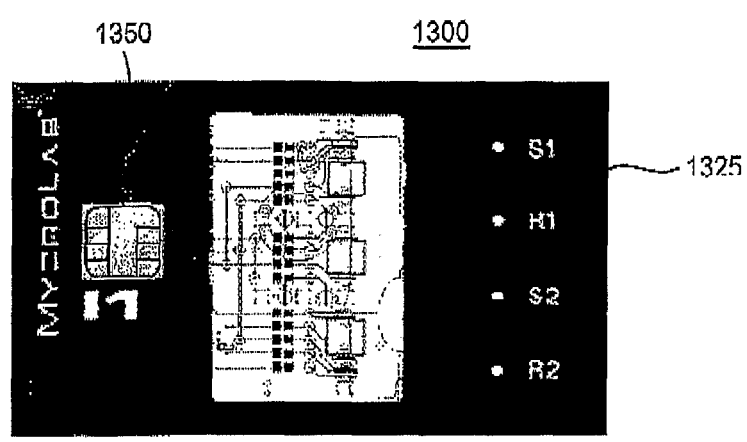

FIGS. 13A-13E illustrate composite images of a consumable device 1300 fabricated by multilayered components and having a configuration similar to the consumable device 805, shown in FIG. 8. FIG. 13A shows top graphic and interface layers 1305, FIG. 13B shows electrical layers 1310, FIG. 13C shows fluidic layers 1315, FIG. 13D shows bottom layers 1320, and FIG. 13E shows a top view of all layers 1325, as assembled. In this example, the device 1300 operates in a slave configuration with respect to an external device that provides external commands for controlling other electronic components (e.g., logic, processors, controllers, and sensor or actuator systems), which can be provided on the device 1300. As shown in FIG. 13A, the device 1300 may include a user interface comprising four pushbuttons 1330. As shown in FIG. 13B, the device 1300 may also include sensors 1335 around fluidic ports 1340, as well as data handling components 1345, which provide sensor feedback to an instrument and chip-card electrode module 1350.

In yet another exemplary implementation, a device according to the present invention comprises on-board data handling components that include electronic and/or integrated circuits for autonomous operation (i.e., the device operates independently of other instruments and/or devices). For example, the consumable device 1100, shown in FIG. 11, has on-board data handling circuitry that includes all of the necessary detection systems 1105, process controllers 1110, data storage 1115, power 1120, and control systems 1125, as well as a user interface 1130, for autonomous operation.

Figure 14A:
FIGS. 14A-E illustrate composite images of a multilayer device that is a self-contained instrumentation system, similar to the system shown in FIG. 11.
Figure 14B:
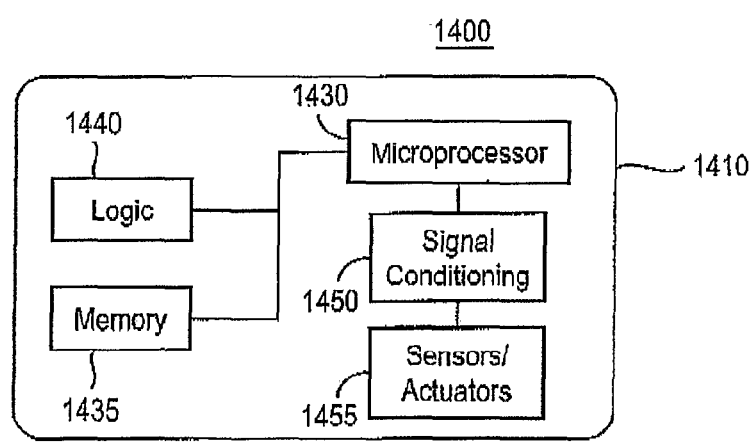
Figure 14C:
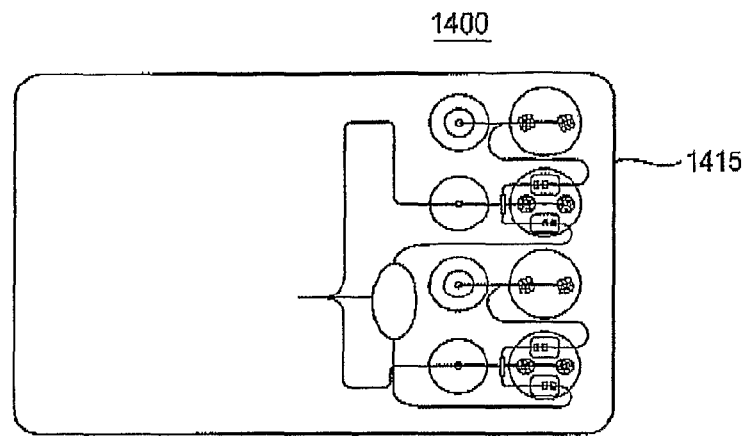
Figure 14D:
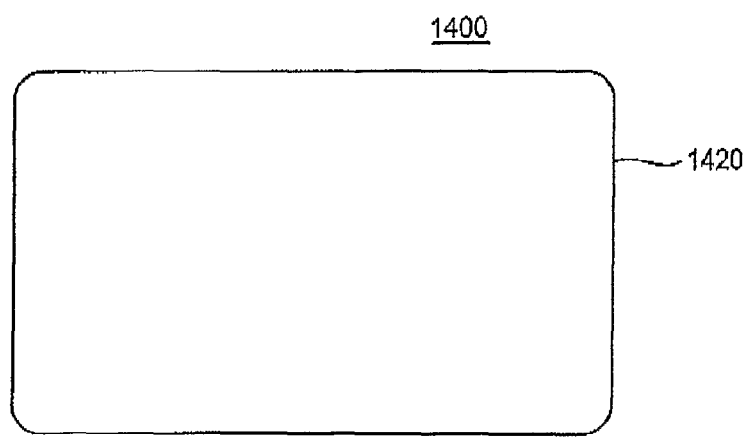
Figure 14E:
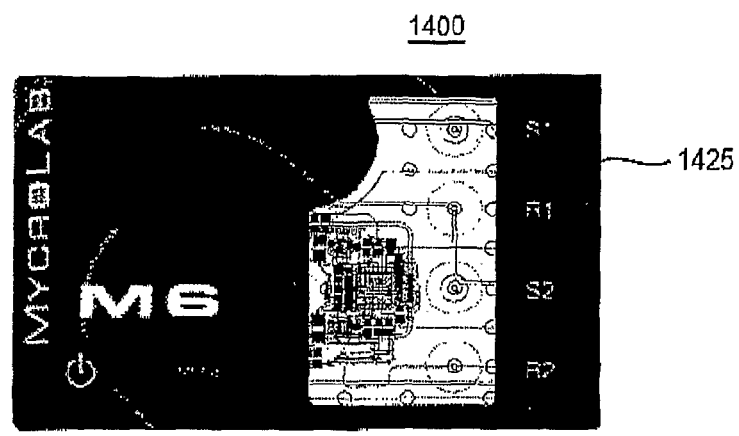

FIGS. 14A to 14E illustrate composite images of a consumable device 1400 fabricated by multilayered components and having a configuration similar to the consumable device 1100, shown in FIG. 11. FIG. 14A shows top graphic and interface layers 1405 of the device 1400, FIG. 14B shows electrical layers 1410, FIG. 14C shows fluidic layers 1415, FIG. 14D shows bottom layers 1420, and FIG. 14E shows a top view of all layers 1425, as assembled. In this example, the device 1400 contains an on-board microprocessor 1430, memory 1435, logic 1440, user interface 1445, and analog signal conditioning 1450 interfaced to sensors and actuators 1455.

Figure 15C:
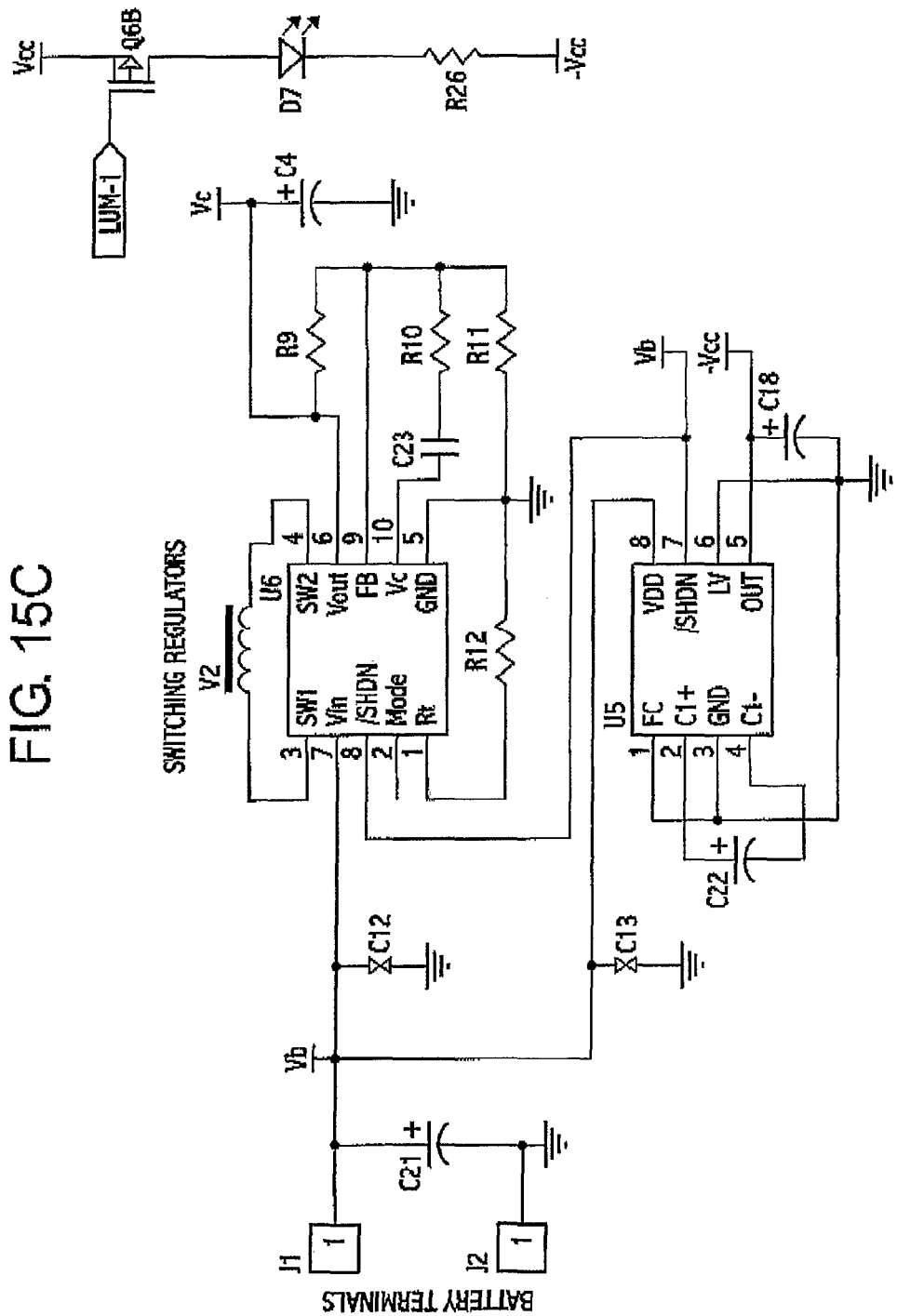
Figure 15D:
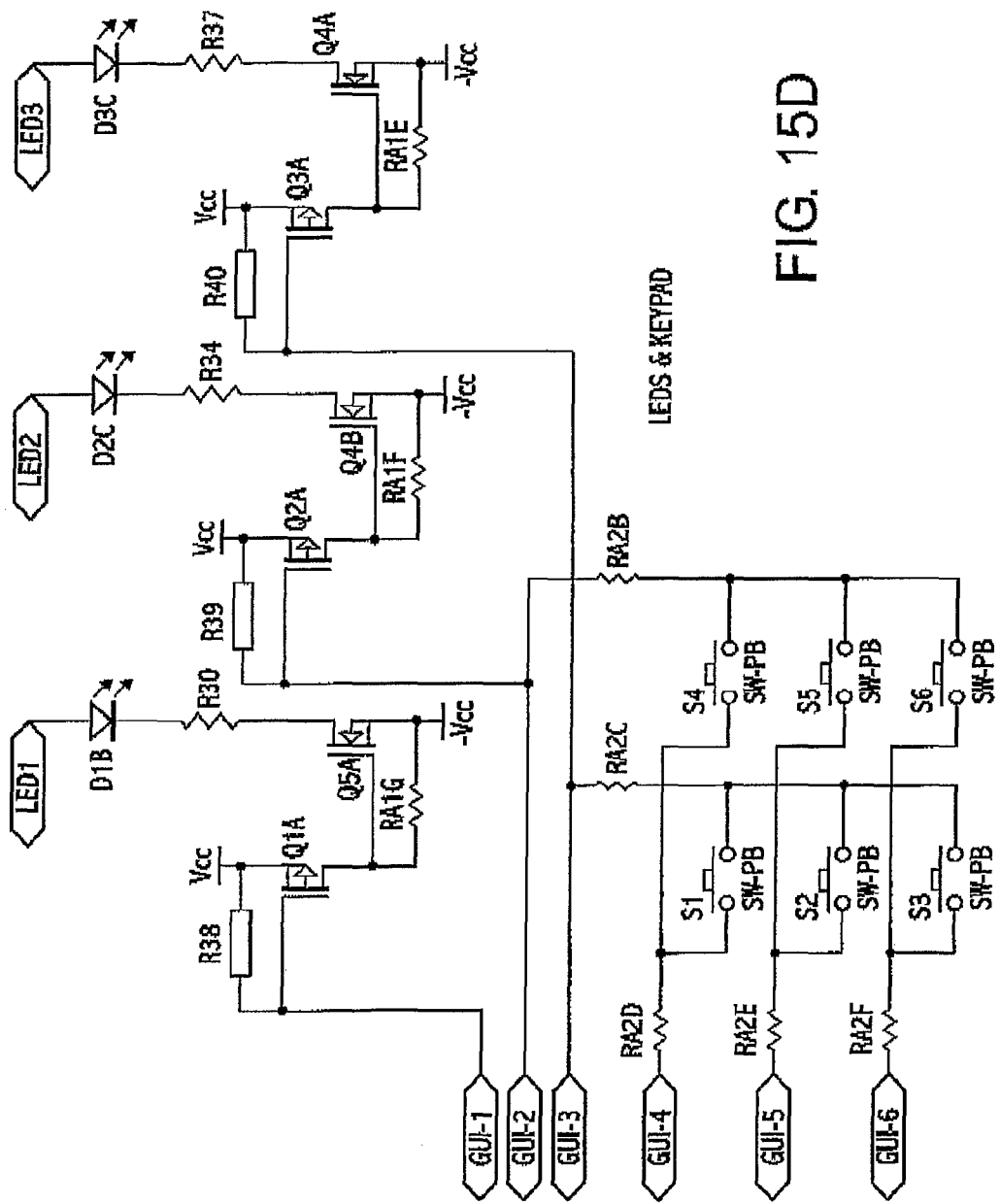
Figure 15E:
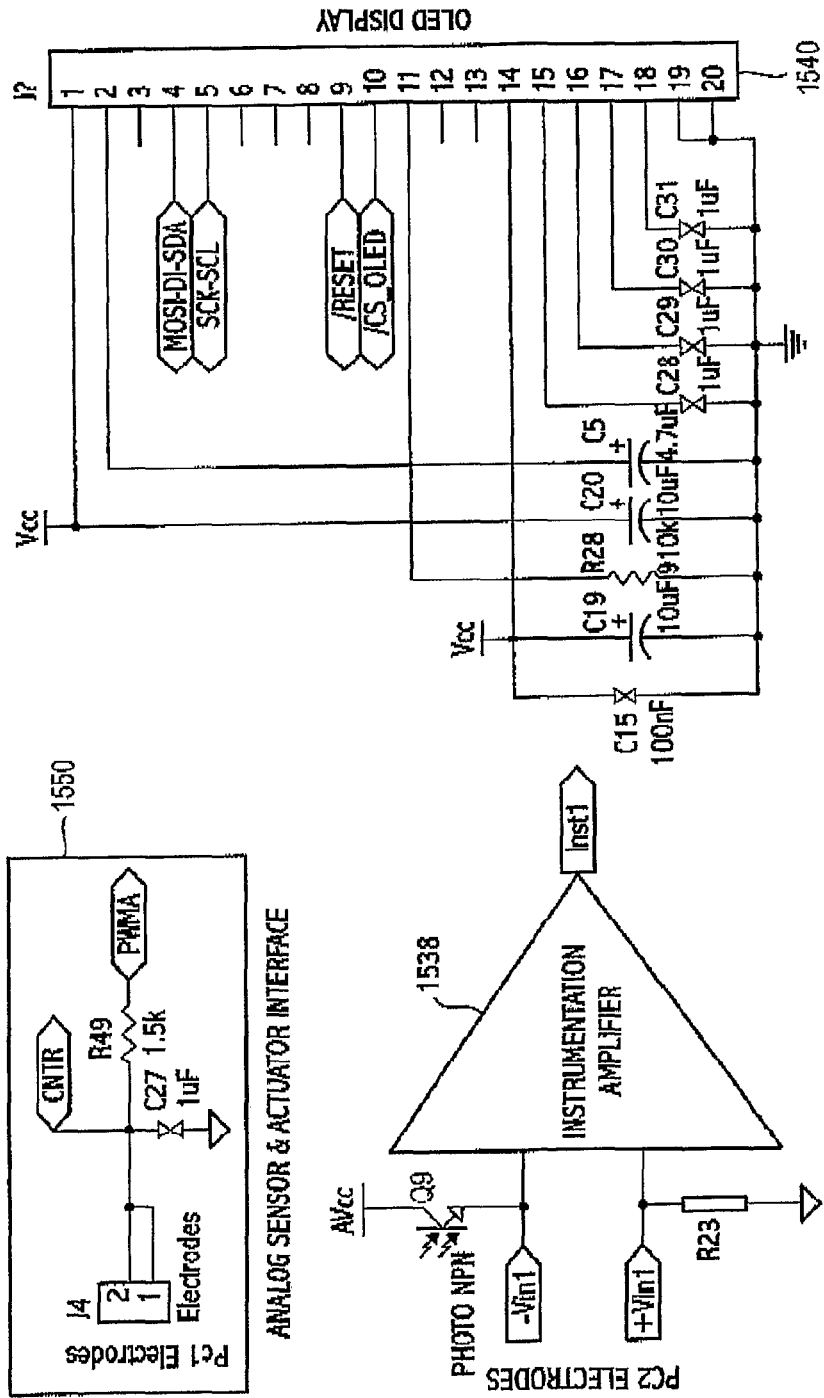
Figure 16:
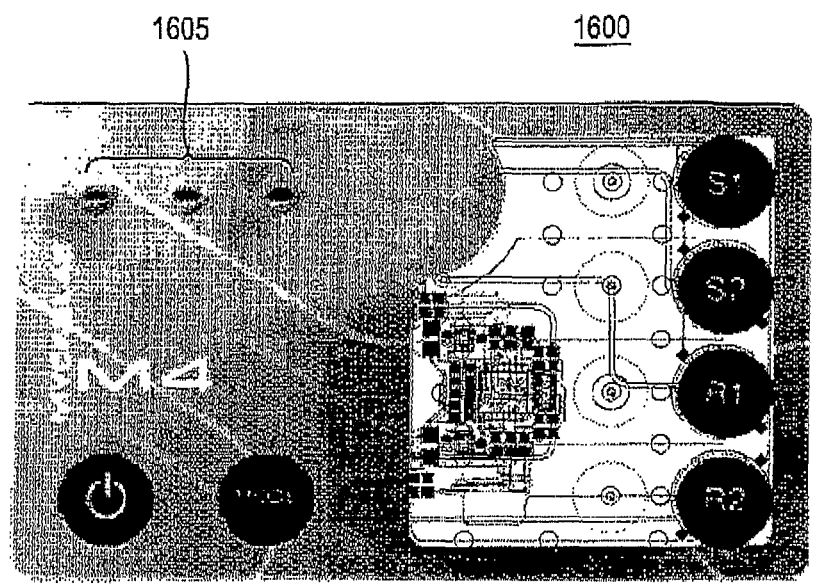
FIG. 16 is a composite image of an exemplary device, similar to the multilayer device shown in FIGS. 14A-E, but having three light-emitting diodes (LEDs) providing visual feedback to a user.

FIGS. 15A-15E illustrate a circuit diagram, of a device 1500 having a configuration similar to that of device 1400. Those skilled in the art will understand that particular components, as well as particular component values are shown for illustrative purposes only, and that the device 1500 could be implemented using other components and/or other component values. The device 1500 can be capable of independent operation and communication with other devices via a communications interface 1510, as shown in FIG. 15B. The device 1500 includes all of the necessary on-board data handling circuitry for autonomous operation, including a microprocessor 1530, memory 1535, and logic 1536, as shown in FIG. 15A, as well as analog signal conditioning 1538 interfaced 1550 to sensors and actuators and a display comprising an OLED matrix 1540, as shown in FIG. 15E. The device 1500 is battery operated, as shown in FIG. 15C, but an external instrument could be connected to the device 1500 to supply power for operation or to place the microprocessor 1530 in Reset and directly access the memory 1535. FIG. 16 illustrates a composite image of a consumable device 1600 having a configuration similar to that of device 1500, except a user interface of device 1600 comprises an LED display 1605 instead of an OLED matrix 1540.

Figure 17:
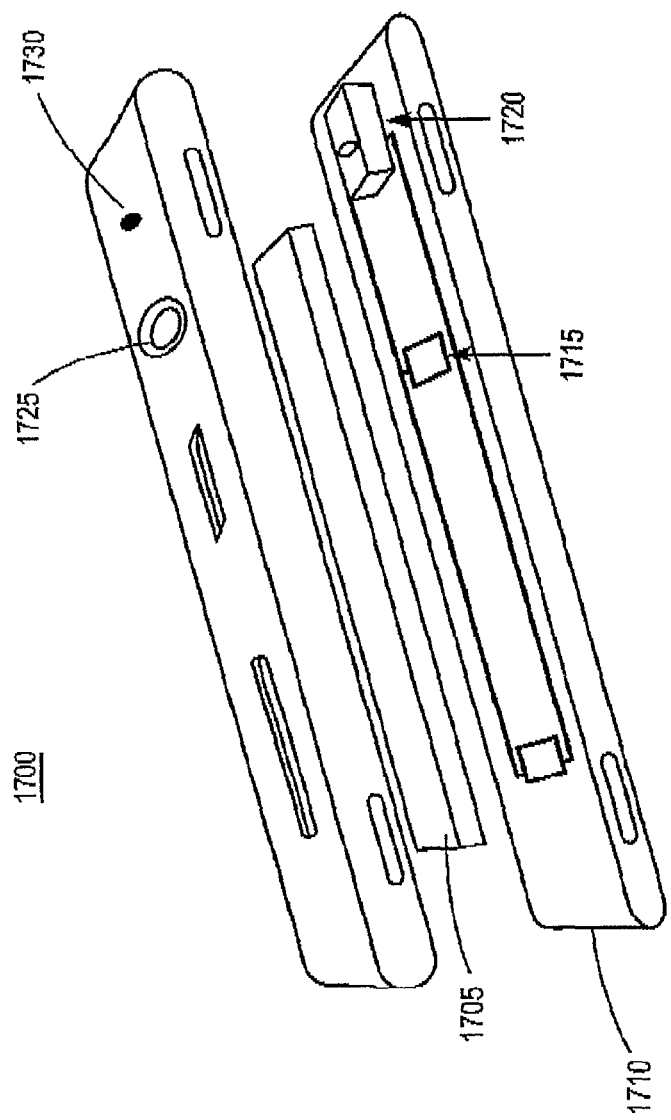
FIG. 17 is a diagram representing an exemplary device that includes electronic circuit, sensor and lateral flow components.
Figure 19A:
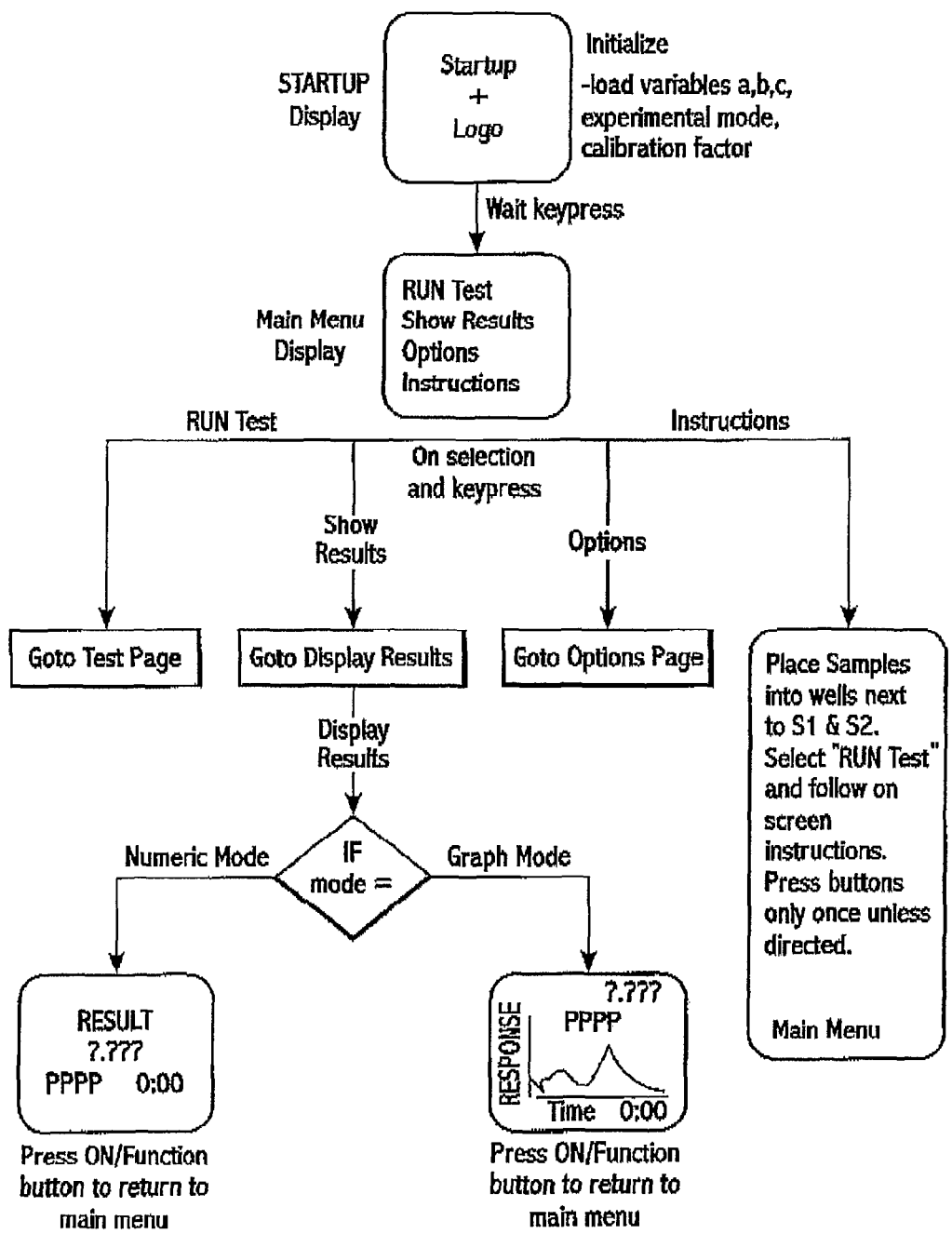
FIGS. 19A-19D provide an exemplary application program flow for the device shown in FIGS. 14A-E.
Figure 19B:
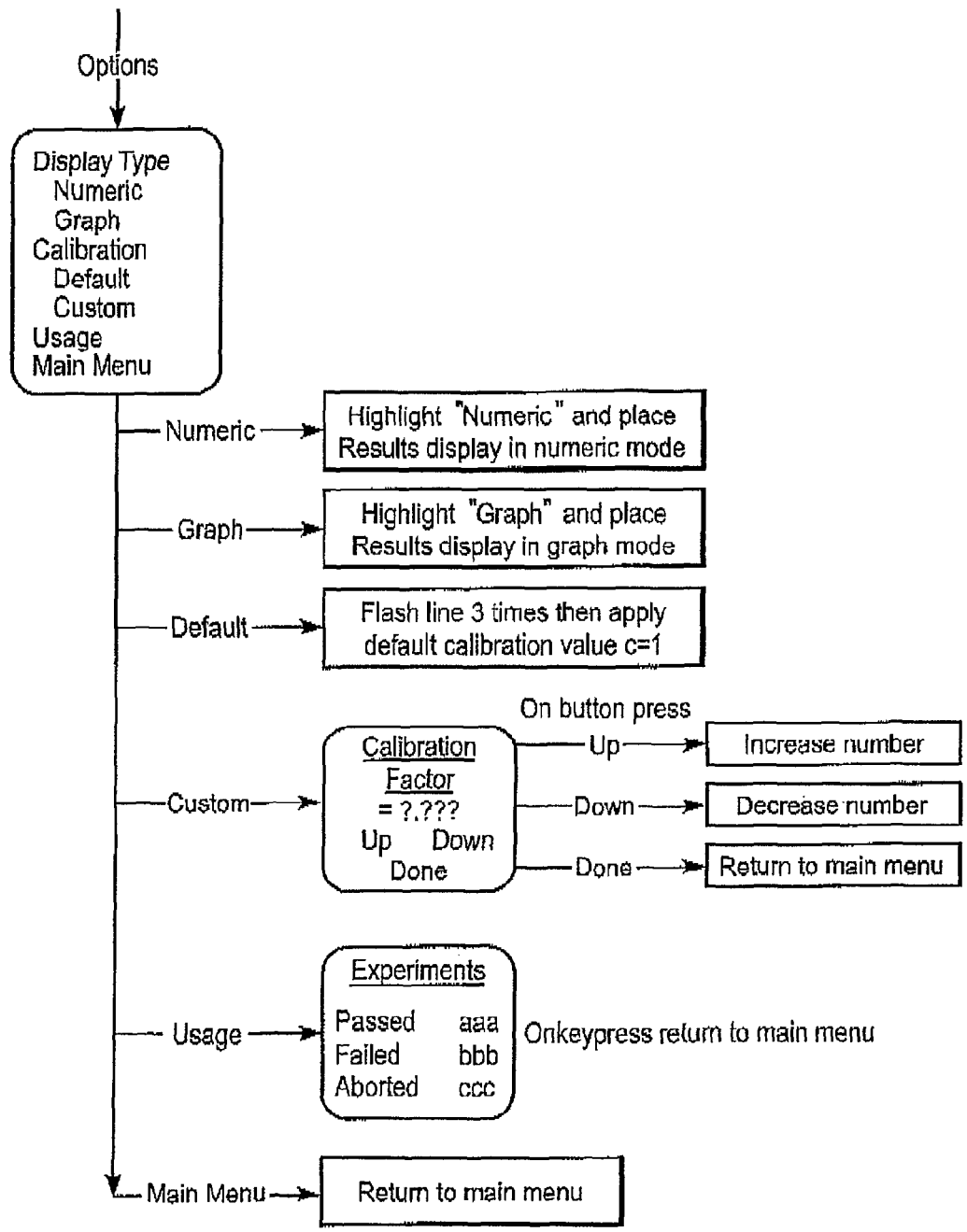
Figure 19C:
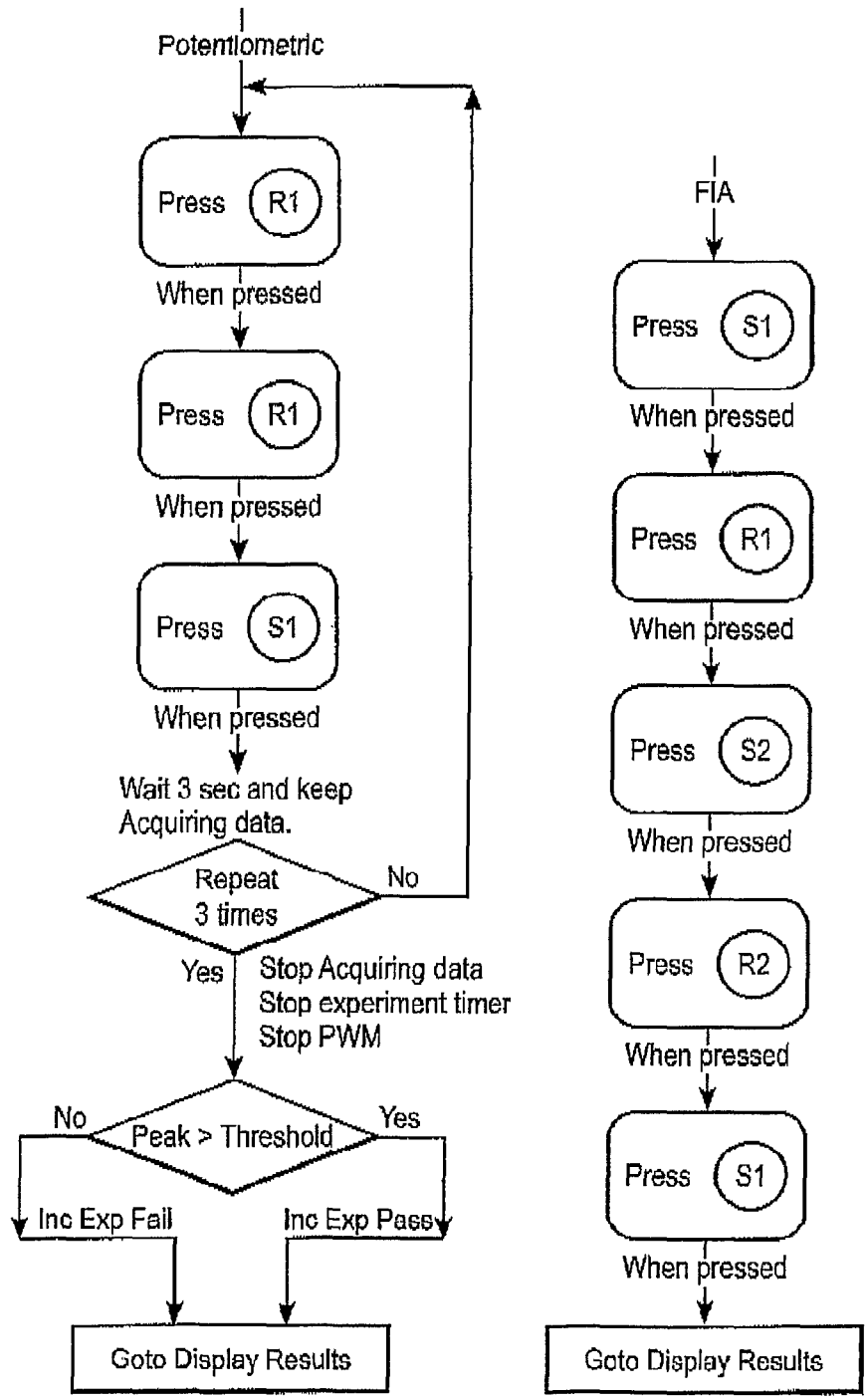
Figure 19D:
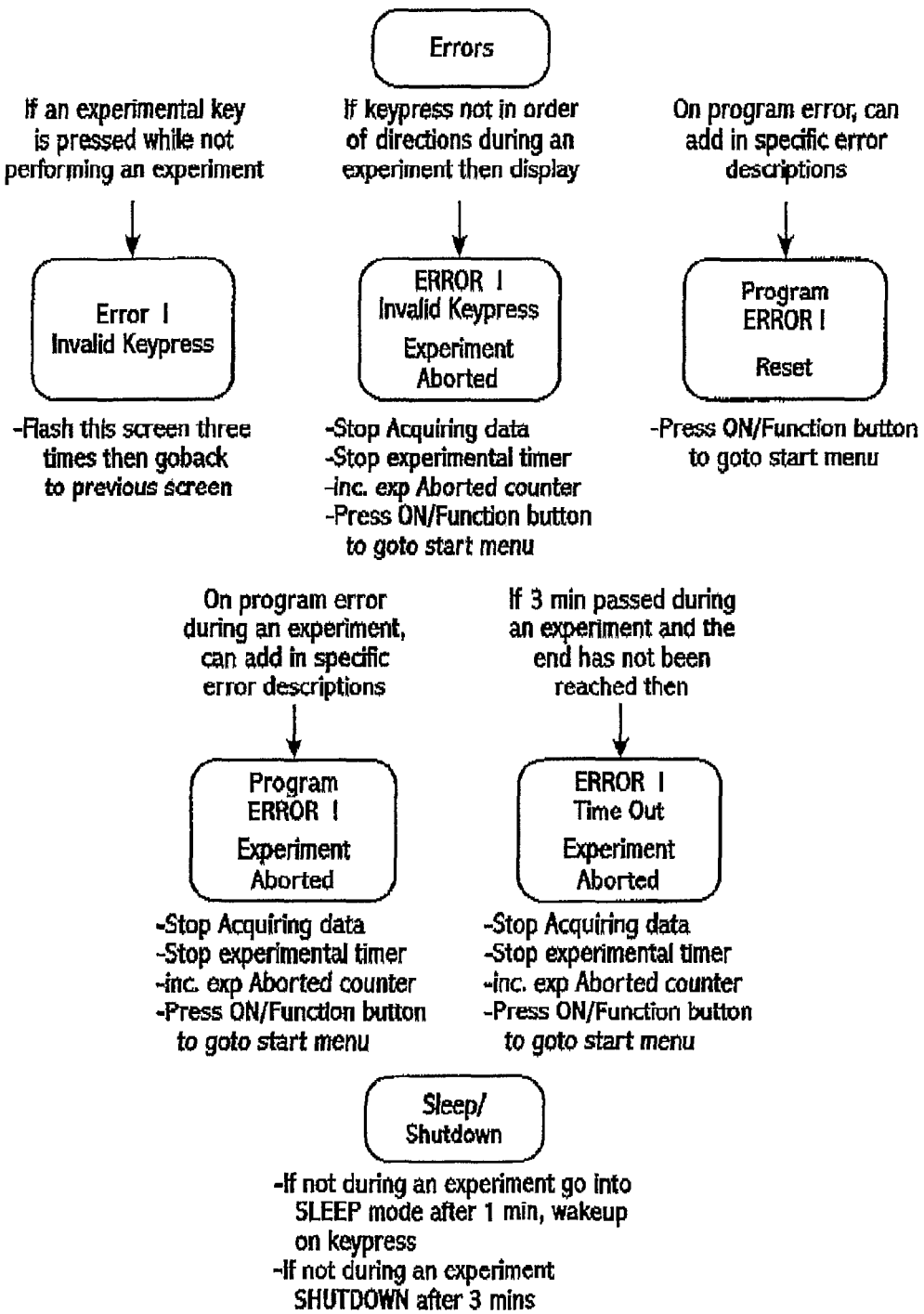

FIG. 17 illustrates an exemplary device 1700 having a configuration similar to the consumable device 1100, shown in FIG. 11. The device 1700 may include fluid handling components, such as lateral flow components 1705 and housings 1710, with on-board sensors 1715 and/or circuitry 1720 to provide functionality. By way of example only, conductivity sensors can be used at a sample inlet 1725 to detect the introduction of a sample into the device 1700 and start an experimental timer, and to ensure that the sample has travelled appropriately along the length and breadth of the test strip 1705 at or past a detection point. The device 1700 can further include an indicator light 1730, or display, to provide information to a user on the validity of an experiment, and a communicator to communicate with other devices and/or instruments. The on-board data-handing components can store other information, such as test result, time and date, identification, manufacturing, and patient information, or can restrict access or disable the device to prevent use. Optical and other electrical sensors may also be used as part of an on-board detection system to increase the sensitivity and reliability of such devices.

According to another aspect of the present invention, RFID systems may be integrated in any suitable way with device components for various purposes, including purposes other than identification. By way of example only, an electrochemical sensor may be connected to a RF transponder either directly or indirectly though a controller, such as a microprocessor, for communication of data to and from an external instrument for purposes described herein. In one exemplary implementation, the RFID component can communicate with an internal sensor system to monitor characteristics of a device or a test. For example, FIG. 18 illustrates a block diagram of a consumable device 1800 having on-board data handling circuitry that includes a processor and control module 1805 interfaced to sensor and/or actuator components 1810. The device 1800 incorporates an RFID antenna 1815 that may be used for communication and/or supply of power 1820.

According to another aspect of the present invention, a device for performing at least part of ah analytical process comprises on-board data handling components that include electronic and/or integrated circuits to perform various other functions, such as protocol automation, control, and monitoring; access and security control; data handling of operational information, results, calibration information, manufacturing data, factory settings, application information, device usage, user settings, sample data, time and date information, location information, environmental monitoring, and other Quality Control and Quality Assurance information. For example, International Patent Application PCT/TB2006/003311 describes exemplary electronic and/or integrated circuits that perform a function whereby all, or some, of the upgrade information, operational data, or software architecture for an instrument can be contained within the device.

According to another optional aspect of the present invention, a device for performing at least part of an analytical process comprises a communicator that includes at least one of a user interface or an instrument interface.

In some embodiments, a device for performing at least part of an analytical process comprises a communicator that includes a user interface enabling any suitable user interaction, such as button pressing and/or reagent addition, in addition to more complex interactions, such as infra-red, or sound (e.g., commands via voice recognition). In an exemplary implementation, the device includes a user interface having elements that can display operational information to the user, such as instructions for a correct operative sequence of button presses. Such a device can also internally monitor the progress of an experiment to ensure validity. For example, the device may monitor button presses to ensure that the buttons are pressed in the correct sequence or that experimental parameters remain within specified limits.

Figure 20:
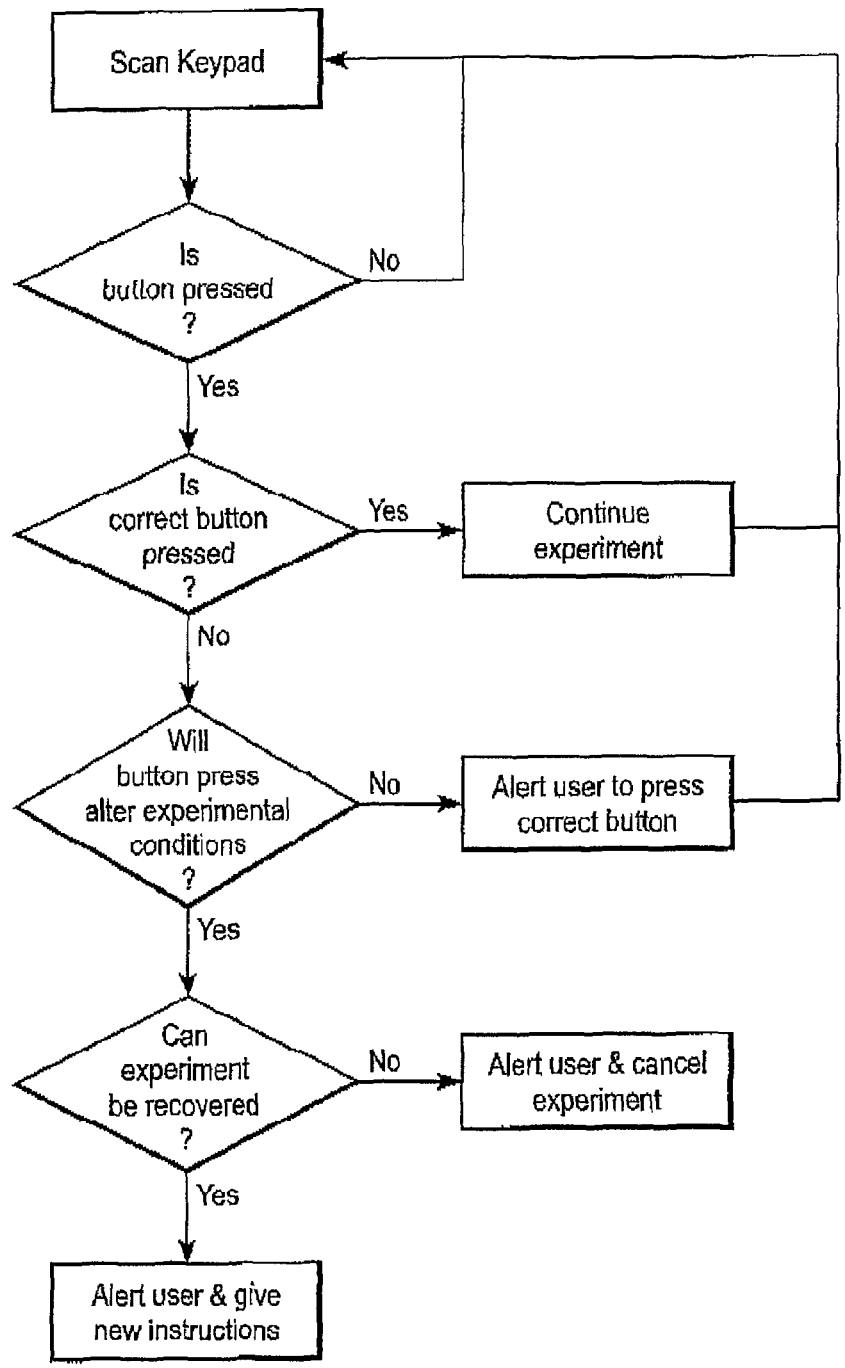
FIG. 20 illustrates a program flow for an exemplary subroutine that monitors keypads to ensure the validity of an experiment.

Consumable devices 1300, 1400 and 1600, shown in FIGS. 13A, 14A and 16, include exemplary user interfaces. As described herein, the device 1300 of FIG. 13A includes a user interface comprising four pushbuttons 1330, and registers button presses and sends the data to another device for user display, whereas the device 1400 of FIG. 14A includes a user interface 1445 comprising push buttons and an OLED graphical display and the device 1600 of FIG. 16 includes a user interface 1605 comprising three tri-colored LED display elements to instruct the user and/or register button presses. FIGS. 19A-19D illustrate an exemplary program flow 1900 at the application level of the device 1400 depicted in FIGS. 14A-14E. FIG. 20 illustrates an exemplary program flow of a subroutine 2000 that scans keypads for user input.

In some embodiments, a device for performing at least part of an analytical process comprises a communicator that includes an instrument interface capable of interfacing with an instrument and, in some cases, providing instructions to the instrument. In an exemplary implementation, the device can enable the instrument to monitor the progress of device operation. Such a feature is useful, for example, to assist in automated system operation and may be useful, for example, in automating a current protocol for the user and/or providing instructions to the user.

As described herein, a device according to the present invention can perform at least part of an analytical process, including, but not limited to, data storage and testing functions, such as physical, chemical and/or biochemical processing, monitoring, and/or analysis. The monitoring, control, collection, storage, manipulation, and/or transmission of data in devices and systems according to the present invention may occur during an experiment and/or at other times.

Figure 21:
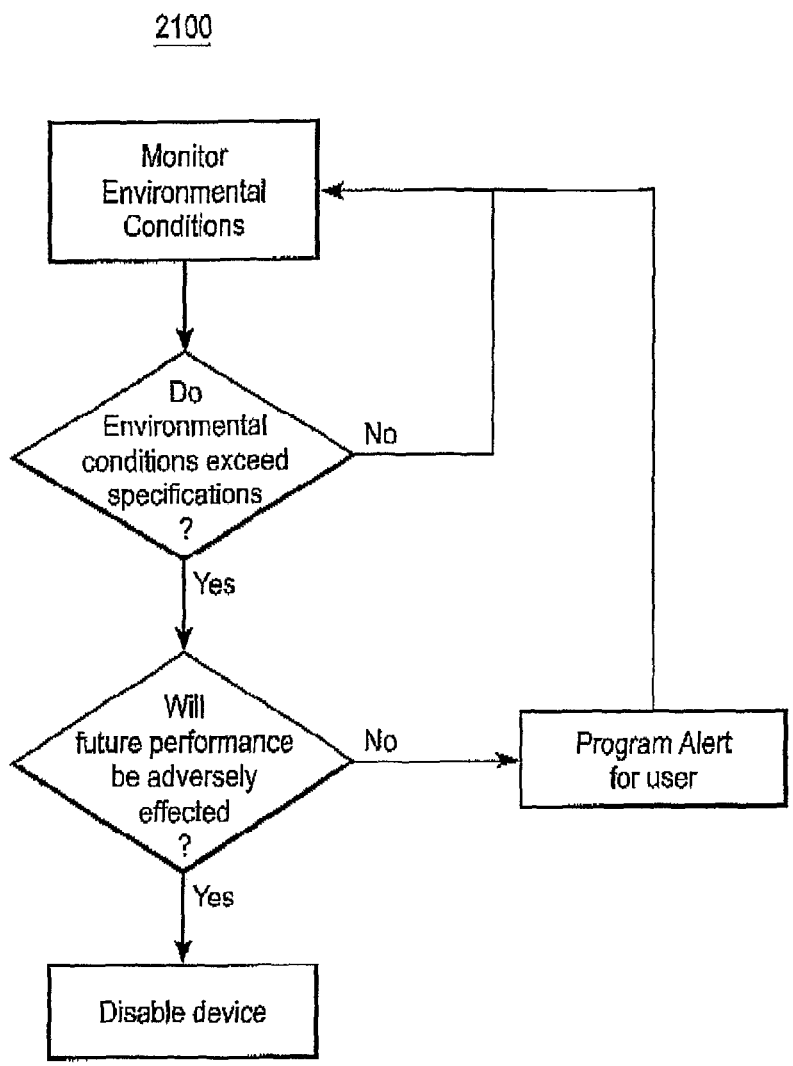
FIG. 21 illustrates a program flow for an exemplary subroutine that monitors a device during storage and transit to ensure that the device is not used under certain conditions.

In an embodiment, a device for performing at least part of analytical process according to the present invention may monitor and/or control its environment and/or internal functions both during and outside an experimental operation. FIG. 21 depicts an exemplary program flow 2100 of a device for monitoring its environmental conditions. In this example, if environmental conditions exceed operational parameters, then an alert can be given and/or the device can be rendered inoperable.

Figure 22:
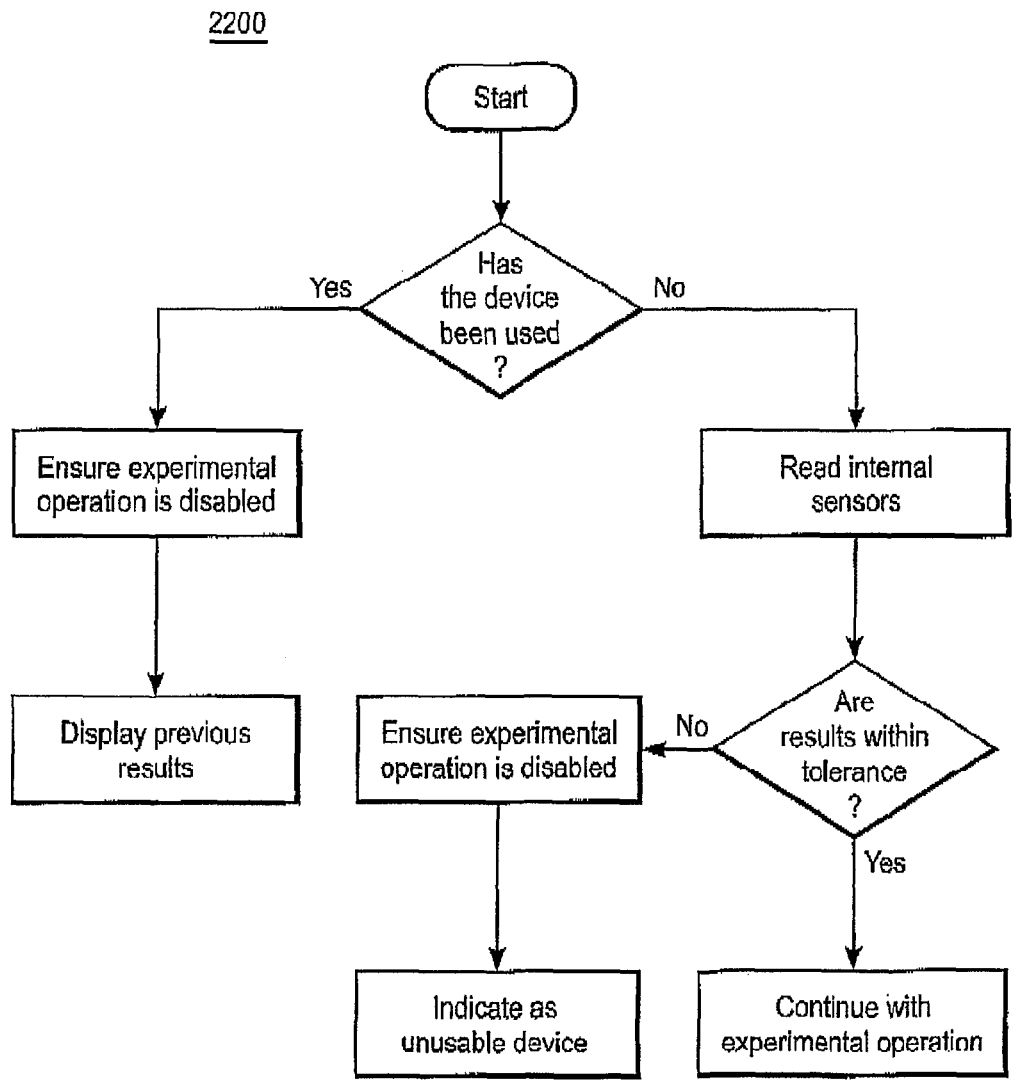
FIG. 22 illustrates a program flow for an exemplary subroutine that monitors the internal quality of device components and disables the device under certain conditions.

In another embodiment, a device for performing at least part of analytical process according to the present invention, may perform internal quality control monitoring to reduce the need for external testing. For example, individual devices can be monitored internally and the results stored on the device and/or transmitted to a database. Such monitoring may be of any suitable type, relating to, for example, quality control tracking of manufacturing parameters, environmental conditions, and operator usage and time, among others. FIG. 22 depicts an exemplary program flow 2200 of a device for preventing the device from performing an experiment on start-up if an experiment was previously performed with the device or if reagents or sensors are no longer within a specified tolerance.

In another embodiment, a device for performing at least part of analytical process according to the present invention may perform security applications. For example, electronic and/or integrated circuits may be implemented to restrict access to or use of the device or an associated instrument under certain conditions. In this case, access may be restricted if data is entered incorrectly, if correct access codes or user ID are not provided, or during certain periods of operation (e.g., before or during a critical point in a testing procedure). The device can be configured to perform other security functions, such as warning, data verification, data encryption, and dongle protection functions, among others.

Figure 23:
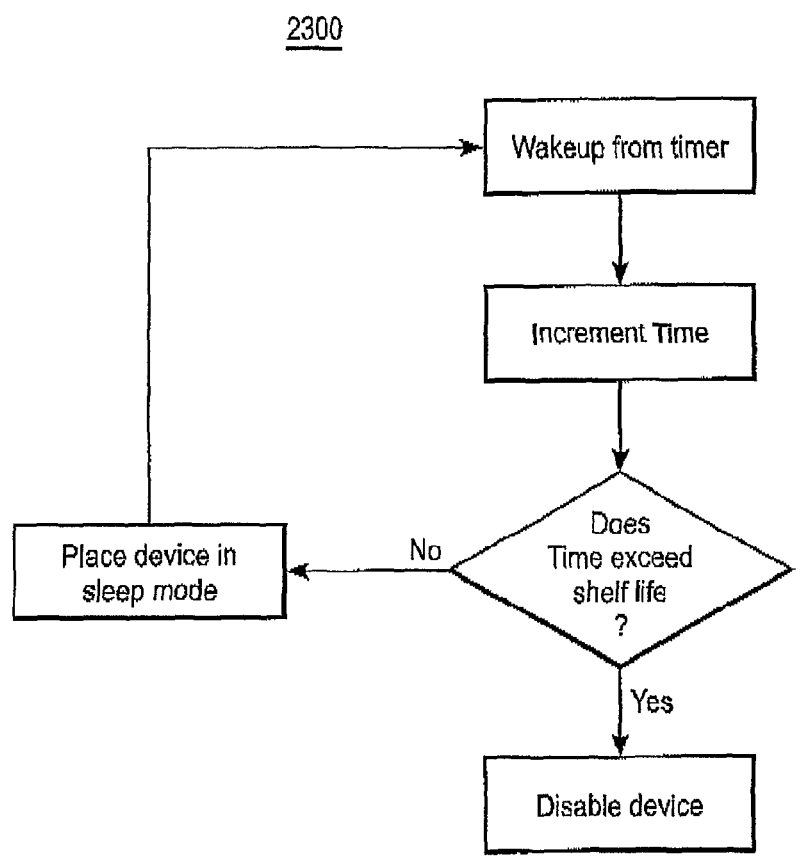
FIG. 23 illustrates a program flow for an exemplary subroutine that monitors the age of a device and disables the device under certain conditions.

In another embodiment, a device for performing at least part of analytical process according to the present invention may alter data, results, a user interface, or operation of the device under certain conditions. For example, electronic and/or integrated circuits may be implemented to render results unreadable if they are not used, read, or interacted with within a certain timeframe. FIG. 23 depicts an exemplary program flow 2300 for a device in which the age of the device is monitored and the device is disabled when the age exceeds a specified shelf life.

In another embodiment, a device for performing at least part of analytical process according to the present invention may perform remote monitoring and/or control. For example, the device may be used for environmental monitoring in remote locations for extended periods. In this case, the device can be configured with a dry reagent battery that becomes active upon introduction of aqueous samples that wet the galvanic cell of the battery, thereby allowing electrical conduction and device activation.

In another embodiment, a device for performing at least part of analytical process according to the present invention, may store data over single or multiple sampling periods. Such data might include test results, manufacturing, experimental, user, and/or other data. For example, such data storage capability can enable, among other features, tracing of the device and its history and monitoring over extended time periods without data transfer to an external instrument.

In another embodiment, a device for performing at least part of analytical process according to the present invention may perform part of a verification or calibration procedure. The device may supply calibration information and/or perform an internal calibration, for example, on its internal electronic, sensor and/or actuator systems. The device may also supply calibration information and/or perform a calibration externally, for example, on instruments, electronics, sensors and/or actuator systems. In one implementation, an interfaced instrument may measure fixed, known values of the device, such as resistive loads, voltage, and/or current generators, as part of a calibration procedure. In another implementation, the device may store data about the calibration of its on-board sensors in memory for use by an interfaced instrument. Optionally, an interfaced instrument may also store calibration information and/or perform calibrations on the device.

Figure 24:
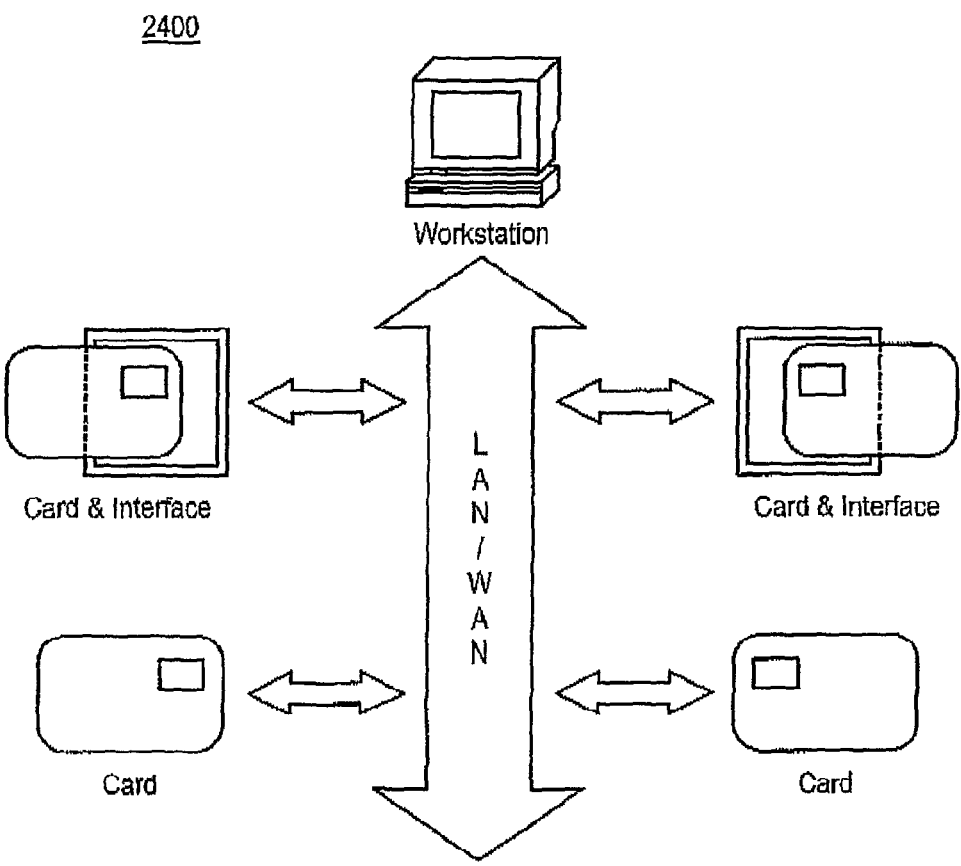
FIG. 24 illustrates an exemplary distributed local area network (LAN) or wide area network (WAN) of devices.
Figure 25:
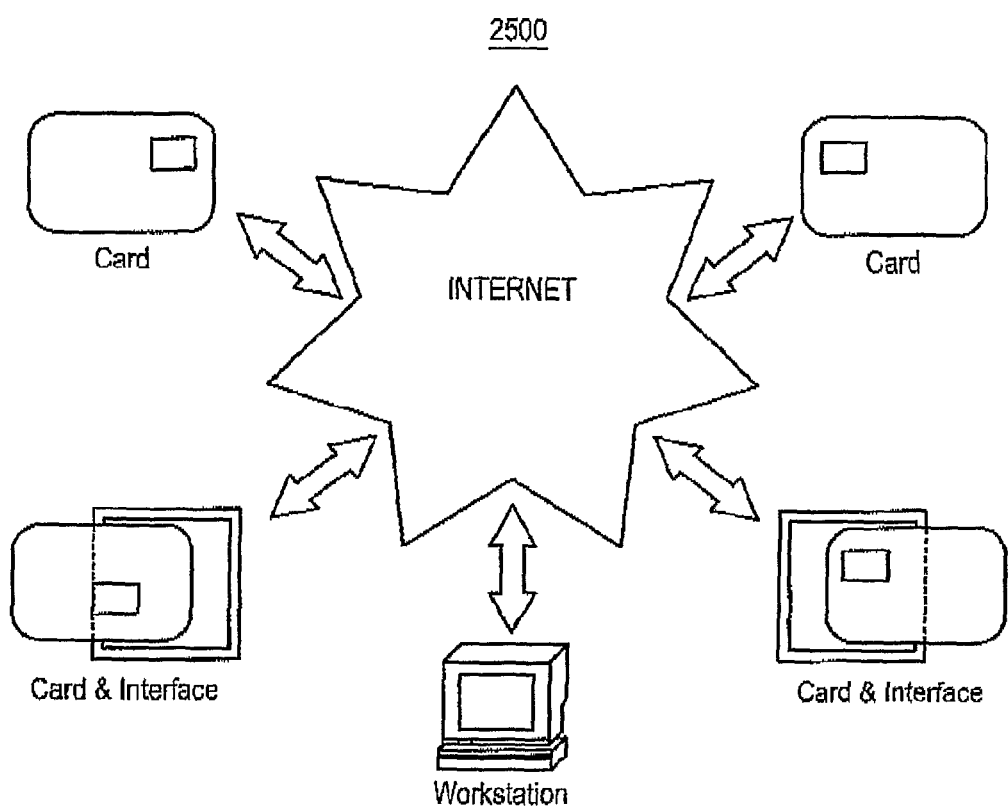
FIG. 25 illustrates an exemplary distributed network of devices interfaced to the internet.

In another embodiment, devices for perforating at least part of an analytical process in accordance with the present invention form part of a distributed network (e.g., wired and wireless LANs, WANs, dedicated networks, intranets, the internet, etc.) and may perform medical, industrial and consumer diagnosis, monitoring and/or control applications, among others. For example, FIG. 24 illustrates an exemplary network 2400 of devices for performing at least part of an analytical process in which the devices communicate over a LAN/WAN. FIG. 25 illustrates an exemplary network 2500 of devices for performing at least part of an analytical process in which the devices communicate over the internet. Devices may interface with the network in any suitable way, for example, via an instrument or directly into the network or a network access point. In one implementation, the devices may operate independently and communicate with each other or to another point on the network. In another implementation, a device can operate as part of a distributed instrument where some or all of the control and/or data processing is performed remotely from the device. An advantage of this configuration is distributed, low-cost, high-performance sensor devices can be provided with high-end data processing and GUI being provided by one or more networked instruments. In one embodiment, the devices include on-board sensors.

Figure 26:
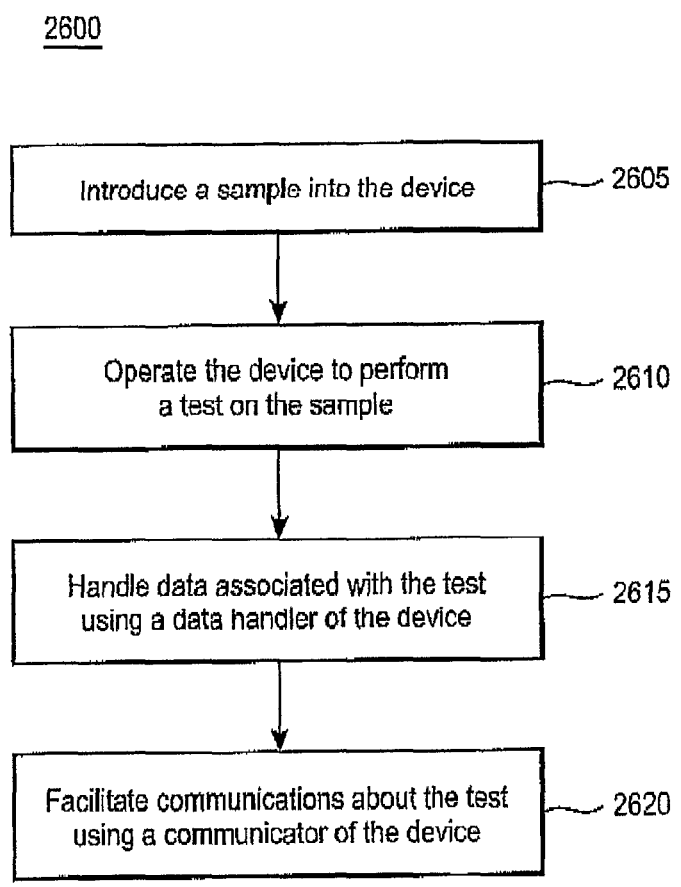
FIG. 26 illustrates a process flow of an exemplary method for performing at least part of an analytical process using a device according to the present invention.

In an illustrative embodiment, a device according to the present invention can be used to perform at least part of an analytical process. For example, FIG. 26 illustrates a process flow of on exemplary method 2600 for performing at least part of an analytical process using a device according to the present invention. In step 2605, a sample is introduced into the device. For example, the sample may comprise a substance with biological matter drawn from a body, such as DNA, or the sample may comprise a chemical or biological sample for environmental, industrial, agricultural, horticultural, food safety, forensic, veterinary, medical, bio-security, pharmaceutical, research, identification, or other sample analysis applications. In step 2610, the device is operated to perform a test on the sample. For example, the device might include a sensor that measures an aspect of the sample. In step 2615, a data handler of the device handles data associated with the test. For example, the data handler might store or process the data associated with the test. In step 2620, a communicator of the device facilitates communications about the test. For example, the communicator might comprise a user interface having display elements, such as indicator lights, that indicate whether the test was performed properly. The communicator may facilitate communications about the test at any time prior to, during or after performance of the test.

Throughout this specification (including the claims, which follow), unless the context requires otherwise, the word "comprise," and variations such as "comprises" and "comprising," will be understood to imply the inclusion of a stated integer or step or group of integers or steps but not the exclusion of any other integer or step or group of integers or steps.

Numbers expressing quantities of ingredients, constituents, reaction conditions, and so forth used in this specification are to be understood as being modified in all instances by the term "about."

Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques.

The reference to any prior art in this specification is not, and should not be taken as, an acknowledgement or any form of suggestion that the prior art forms part of the common general knowledge.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims. It is intended that all such modifications and alterations be included insofar as they come within the scope of the invention as claimed or the equivalents thereof.

What is claimed is:

1. A consumable device for performing at least part of an analytical process comprising: a communicator configured to facilitate communication with the device; at least one sensor or actuator pertaining to the analytical process on the device connected within the device directly to a data handler;
    wherein the device is a microfluidic device;
    wherein the data handler includes a Smart Card module with an integrated circuit;
    wherein the data handler provides independent control of the at least one actuator component, or the data handler provides measurement of the at least one sensor component;
    wherein the data handler is configured to operate in accordance with a protocol for providing a software or firmware upgrade to the device or to an instrument upon communication with the device.

2. A device according to claim 1, wherein the at least one sensor or actuator is configured as part of an on-board verification or calibration procedure.

3. A device according to claim 1, comprising a data storage means for storing data of the analytical process and/or the device.

4. A device according to claim 1, wherein the device is configured to perform internal quality control monitoring.

5. A device according to claim 1, wherein the Smart card module is configured to perform a security access function.

6. A device according to claim 1, wherein the communicator is capable of communicating with a communications network where the device forms part of a distributed network.

7. A consumable device for performing at least part of an analytical process comprising: a communicator configured to facilitate communication with the device; at least one sensor or actuator pertaining to the analytical process on the device connected within the device directly to a data handler;
    wherein the device is a microfluidic device;
    wherein the data handler includes a Smart Card module;
    wherein the data handler provides independent control of the at least one actuator component, or the data handler provides measurement of the at least one sensor component;
    wherein the device includes a user interface having elements that can display operational information to the user.

8. A consumable device for performing at least part of an analytical process comprising: a communicator configured to facilitate communication with the device connected within the device directly to a data handler;
    wherein the device is a microfluidic device;
    wherein the data handler includes a Smart Card module with an integrated circuit;
    wherein the data handler provides processing and decision-making relating to the analytical process;
    wherein the data handler provides control of other devices through the communicator.

9. A device according to claim 8, wherein at least one sensor or actuator is configured as part of an on-board verification or calibration procedure.

10. A device according to claim 8, comprising a data storage means for storing data of the analytical process and/or the device.

11. A device according to claim 8, wherein the device is configured to perform internal quality control monitoring.

12. A device according to claim 8, wherein the Smart card module is configured to perform a security access function.

13. A device according to claim 8, wherein the data handler is configured to operate in accordance with a protocol for providing a software or firmware upgrade to the device or to an instrument upon communication with the device.

14. A device according to claim 8, wherein the device includes a user interface having elements that can display operational information to the user.

15. A device according to claim 8, wherein the communicator is capable of communicating with a communications network where the device forms part of a distributed network.

* * * * *